US009561340B2

(12) United States Patent
Guney et al.

(10) Patent No.: US 9,561,340 B2
(45) Date of Patent: Feb. 7, 2017

(54) HEADGEAR CONNECTION ASSEMBLY FOR A RESPIRATORY MASK ASSEMBLY

(71) Applicant: ResMed Limited, Bella Vista, New South Wales (AU)

(72) Inventors: Memduh Guney, Sydney (AU); Timothy Tsun-Fai Fu, Sydney (AU); Gary Christopher Robinson, Sydney (AU)

(73) Assignee: ResMed Limited, Bella Vista (AU)

( * ) Notice: Subject to any disclaimer, the term of this patent is extended or adjusted under 35 U.S.C. 154(b) by 293 days.

(21) Appl. No.: 14/291,217

(22) Filed: May 30, 2014

(65) Prior Publication Data

US 2014/0261412 A1 Sep. 18, 2014

Related U.S. Application Data

(63) Continuation of application No. 12/801,167, filed on May 26, 2010, now Pat. No. 8,770,197, which is a
(Continued)

(51) Int. Cl.
*A61M 16/06* (2006.01)
*A61M 16/08* (2006.01)
(Continued)

(52) U.S. Cl.
CPC ......... *A61M 16/0816* (2013.01); *A44B 11/266* (2013.01); *A61M 16/0057* (2013.01);
(Continued)

(58) Field of Classification Search
CPC . A44B 11/266; A61M 16/06; A61M 16/0605; A61M 16/0616; A61M 16/0622; A61M 16/0633; A61M 16/0638; A61M 16/0666; A61M 16/0672; A61M 16/0683; A61M 16/08; A61M 16/0816; A61M 2205/02; A61M 2210/0618; Y10T 24/45524; Y10T 24/45529; Y10T 24/45581
(Continued)

(56) References Cited

U.S. PATENT DOCUMENTS 1,081,745 A 12/1913 Johnston
4,150,464 A 4/1979 Tracy
(Continued)

FOREIGN PATENT DOCUMENTS

AU A-41786/93 2/1994
AU A-30813/97 2/1998
(Continued)

OTHER PUBLICATIONS

Office Action issued in related Chinese Appln. No. 201010119450.4 dated Jan. 30, 2015, with English translation thereof.
(Continued)

*Primary Examiner* — Annette Dixon
(74) *Attorney, Agent, or Firm* — Nixon & Vanderhye P.C.

(57) ABSTRACT

A respiratory mask assembly for delivering breathable gas to a patient includes a frame having a main body and a side frame member provided on each lateral side of the main body. The main body provides an orifice therethrough for the introduction of breathable gas into a nasal breathing cavity and a collar that substantially surrounds the orifice. At least one of the side frame members includes an integrally formed locking clip receiver assembly. The frame is formed by molding such that mold components of a mold can be withdrawn along a single plane to separate the mold from the collar and the locking clip receiver assembly.

19 Claims, 23 Drawing Sheets

Related U.S. Application Data continuation of application No. 10/655,603, filed on Sep. 5, 2003, now Pat. No. 7,753,050, which is a continuation-in-part of application No. 10/235,846, filed on Sep. 2, 2002, now Pat. No. 6,823,869.

(60) Provisional application No. 60/424,698, filed on Nov. 8, 2002, provisional application No. 60/467,571, filed on May 5, 2003, provisional application No. 60/317,486, filed on Sep. 7, 2001, provisional application No. 60/342,854, filed on Dec. 28, 2001.

(51) Int. Cl.
*A44B 11/26* (2006.01)
*A61M 16/00* (2006.01)

(52) U.S. Cl.
CPC ........ *A61M 16/06* (2013.01); *A61M 16/0611* (2014.02); *A61M 16/0616* (2014.02); *A61M 16/0633* (2014.02); *A61M 16/0638* (2014.02); *A61M 16/0683* (2013.01); *A61M 16/08* (2013.01); *A61M 16/0825* (2014.02); *A61M 2206/14* (2013.01); *Y10T 24/1391* (2015.01)

(58) Field of Classification Search
USPC ............ 128/205.25, 206.12, 206.21, 206.27, 128/207.11; 24/614, 615, 625
See application file for complete search history.

(56) References Cited

U.S. PATENT DOCUMENTS

| | | | |
|---|---|---|---|
| 4,402,316 A | 9/1983 | Gladberry | |
| 4,414,973 A | 11/1983 | Matheson et al. | |
| 4,569,106 A | 2/1986 | Lovato | |
| 4,577,375 A | 3/1986 | Beaussant | |
| 4,639,982 A | 2/1987 | Kasai | |
| 4,676,241 A | 6/1987 | Webb et al. | |
| 4,688,337 A | 8/1987 | Dillner et al. | |
| 4,712,280 A | 12/1987 | Fildan | |
| 4,713,844 A | 12/1987 | Westgate | |
| 4,793,032 A | 12/1988 | Crowle | |
| 4,907,584 A | 3/1990 | McGinnis | |
| 4,944,310 A | 7/1990 | Sullivan | |
| 4,960,121 A | 10/1990 | Nelson et al. | |
| 4,991,272 A * | 2/1991 | Bianchi ................ A44B 11/266 24/313 |
| 5,027,481 A | 7/1991 | Frano | |
| 5,069,205 A | 12/1991 | Urso | |
| 5,222,279 A | 6/1993 | Frano et al. | |
| 5,243,971 A | 9/1993 | Sullivan et al. | |
| 5,245,995 A | 9/1993 | Sullivan et al. | |
| 5,291,880 A | 3/1994 | Almovist et al. | |
| 5,441,046 A | 8/1995 | Starr et al. | |
| 5,465,506 A | 11/1995 | Matis et al. | |
| 5,507,076 A | 4/1996 | Anscher | |
| 5,551,131 A | 9/1996 | Anscher | |
| 5,555,569 A | 9/1996 | Lane | |
| 5,590,444 A | 1/1997 | Krauss | |
| 5,657,493 A | 8/1997 | Ferrero et al. | |
| 5,704,345 A | 1/1998 | Berthon-Jones et al. | |
| 5,737,810 A | 4/1998 | Krauss | |
| 5,791,026 A | 8/1998 | Anscher | |
| 5,921,239 A | 7/1999 | McCall et al. | |
| 6,061,883 A | 5/2000 | Uehara | |
| 6,112,746 A | 9/2000 | Kwok et al. | |
| 6,119,693 A | 9/2000 | Kwok et al. | |
| 6,341,710 B1 | 1/2002 | Danielson et al. | |
| 6,347,631 B1 | 2/2002 | Hansen et al. | |
| 6,363,590 B1 | 4/2002 | Lan | |
| 6,374,826 B1 * | 4/2002 | Gunaratnam ......... A61M 16/06 128/206.21 |
| 6,378,466 B1 | 4/2002 | Oyster et al. | |
| 6,412,487 B1 | 7/2002 | Gunaratnam et al. | |
| 6,422,238 B1 | 7/2002 | Lithgow | |
| 6,460,232 B2 | 10/2002 | Maruoka | |
| 6,530,373 B1 | 3/2003 | Patron et al. | |
| 6,532,961 B1 * | 3/2003 | Gunaratnam ......... A61M 16/06 128/205.25 |
| 6,536,435 B1 | 3/2003 | Fecteau et al. | |
| 6,611,965 B1 | 9/2003 | Lee | |
| 6,615,460 B1 | 9/2003 | Baumgarten | |
| D485,905 S | 1/2004 | Moore et al. | |
| 6,684,466 B2 | 2/2004 | Nishida et al. | |
| 6,796,308 B2 | 9/2004 | Gunaratnam et al. | |
| 6,823,869 B2 | 11/2004 | Raje et al. | |
| 6,907,882 B2 | 6/2005 | Ging et al. | |
| 6,986,352 B2 | 1/2006 | Frater et al. | |
| 7,111,368 B2 | 9/2006 | Matoba | |
| 7,290,313 B2 | 11/2007 | Southern | |
| 7,487,772 B2 | 2/2009 | Ging et al. | |
| 7,597,100 B2 | 10/2009 | Ging et al. | |
| 7,753,050 B2 | 7/2010 | Lithgow et al. | |
| 7,841,345 B2 | 11/2010 | Guney et al. | |
| 8,763,612 B2 | 7/2014 | Guney et al. | |
| 2001/0010778 A1 | 8/2001 | Hilton et al. | |
| 2002/0029780 A1 | 3/2002 | Frater et al. | |
| 2002/0040514 A1 | 4/2002 | Uehara et al. | |
| 2003/0106192 A1 | 6/2003 | Schmitz | |
| 2003/0110605 A1 | 6/2003 | Nishida et al. | |
| 2003/0135966 A1 | 7/2003 | Tejima | |
| 2003/0196302 A1 | 10/2003 | Buscart | |
| 2003/0196656 A1 | 10/2003 | Moore et al. | |
| 2003/0196658 A1 | 10/2003 | Ging et al. | |
| 2003/0196662 A1 | 10/2003 | Ging et al. | |
| 2004/0045551 A1 | 3/2004 | Eaton et al. | |
| 2004/0112384 A1 | 6/2004 | Lithgow et al. | |
| 2005/0199240 A1 | 9/2005 | Hall | |
| 2008/0066759 A1 | 3/2008 | Howard et al. | |
| 2010/0236559 A1 | 9/2010 | Lithgow et al. | |
| 2010/0275923 A1 | 11/2010 | Guney et al. | |
| 2014/0238404 A1 | 8/2014 | Guney et al. | |

FOREIGN PATENT DOCUMENTS

| | | |
|---|---|---|
| AU | 200175559 | 3/2002 |
| CN | 1307847 | 8/2001 |
| CN | 1345558 | 4/2002 |
| DE | 2 323 633 | 11/1974 |
| DE | 29723101 U1 | 7/1998 |
| DE | 100 57 893 C1 | 7/2002 |
| EP | 0 471 264 | 2/1992 |
| EP | 1 166 674 A1 | 1/2002 |
| EP | 1 356 843 | 10/2003 |
| FR | 2 676 652 | 11/1992 |
| GB | 1146568 | 3/1969 |
| GB | 2 002 445 | 2/1979 |
| GB | 2150632 | 7/1985 |
| JP | 6-38810 | 2/1994 |
| JP | 8-22242 | 3/1996 |
| JP | H09-502628 | 3/1997 |
| JP | 10-117814 | 5/1998 |
| JP | 10-327908 | 12/1998 |
| JP | 11-309004 | 11/1999 |
| JP | 2001-178506 | 7/2001 |
| JP | 2001-218606 | 8/2001 |
| JP | 2002-51824 | 2/2002 |
| JP | 2003-129325 | 5/2003 |
| JP | 2004-000574 | 1/2004 |
| WO | WO 85/01192 | 3/1985 |
| WO | WO 98/12965 | 4/1998 |
| WO | WO 99/35933 | 7/1999 |
| WO | WO 99/61088 | 12/1999 |
| WO | WO 00/78383 | 12/2000 |
| WO | WO 00/78384 | 12/2000 |
| WO | WO 01/32250 | 5/2001 |
| WO | WO 03/082406 | 10/2003 |

(56) References Cited

FOREIGN PATENT DOCUMENTS

WO    WO 03/090827     11/2003
WO    WO 2004/022144    3/2004

OTHER PUBLICATIONS

Patent Examination Report No. 1 issued in corresponding Australian Appln. No. 2015203730 dated Mar. 7, 2016.
U.S. Appl. No. 60/377,254, filed May 2002, Moore et al.
U.S. Appl. No. 60/397,195, filed Jul. 2002, Moore et al.
U.S. Appl. No. 60/402,509, filed Aug. 2002, Moore et al.
U.S. Appl. No. 10/655,603, filed Sep. 2003, Lithgow et al.
U.S. Appl. No. 60/424,698, filed Nov. 2002, Lithgow et al.
U.S. Appl. No. 60/467,571, filed May 2003, Lithgow et al.
U.S. Appl. No. 60/317,486, filed Sep. 2001, Raje et al.
U.S. Appl. No. 60/342,854, filed Dec. 2001, Raje et al.
Japanese Patent Appln. No. 2004-569776 mailed Dec. 15, 2009, with English translation.
New Zealand Patent Appln. No. 573462, Office Action mailed Dec. 12, 2008.
Japanese Appln. No. 2004-569776, Office Action dated Mar. 3, 2009.
Chinese Appln. No. 03821171.8, Second Office Action dated Oct. 17, 2008.
Office Action in related Australian Application No. 2003257270, dated Mar. 5, 2008.
EP Search Report issued in EP Appln. No. 03793490.8 dated Jun. 23, 2010.
Office Action issued in EP Appln. No. 03793490.8 dated Oct. 20, 2010.
Office Action issued in related Chinese Appln. No. 200910005239.7 dated Dec. 24, 2010, with English translation.
Office Action issued in related Japanese Appln. No. 2009-140432 mailed Aug. 23, 2011, with English translation.
Office Action issued in related Japanese Appln. No. 2009-140432 mailed May 1, 2012, with English translation.
Office Action issued in related European Appln. No. 03 793 490.8 mailed Jul. 31, 2012.
Notice of Allowance issued in corresponding Japanese Appln. No. 2009-140432 mailed Oct. 2, 2012.
Decision of Rejection issued in Chinese Appln. No. 201010119450.4 mailed Nov. 21, 2012, with English translation.
Decision of Rejection issued in corresponding Japanese Appln. No. 2010-279326 mailed Feb. 26, 2013, with English translation.
Office Action issued in related U.S. Appl. No. 14/269,768 dated Sep. 25, 2014.
Patent Examination Report No. 1 issued in corresponding Australian Appln. No. 2013211476 dated Jul. 21, 2014.
Notification of Reexamination issued in related Chinese Appln. No. 201010119450.4 dated May 21, 2014, with English translation thereof.

* cited by examiner

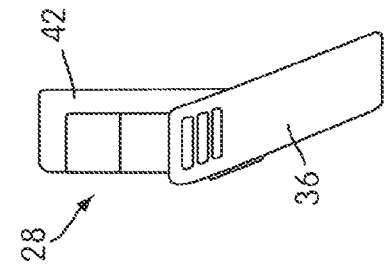
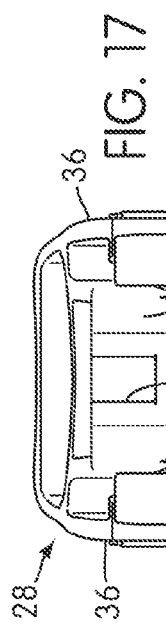
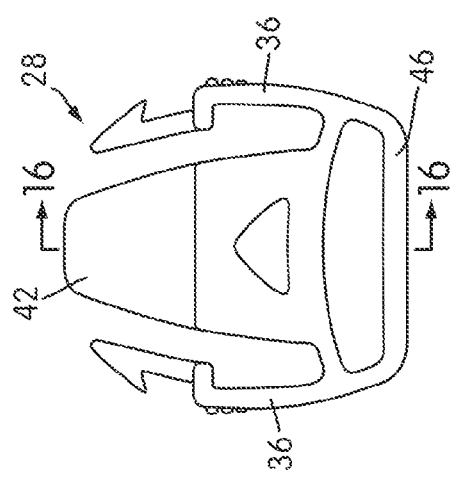
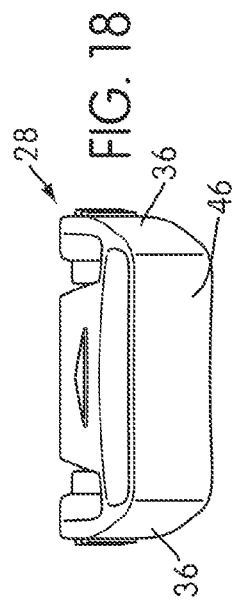
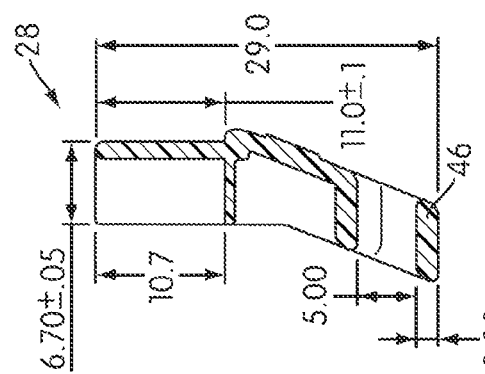

HEADGEAR CONNECTION ASSEMBLY FOR A RESPIRATORY MASK ASSEMBLY

CROSS-REFERENCE TO PRIORITY APPLICATIONS

This application is a continuation of U.S. application Ser. No. 12/801,167, filed May 26, 2010, which is a continuation of U.S. application Ser. No. 10/655,603, filed Sep. 5, 2003, now U.S. Pat. No. 7,753,050, which claims the benefit of U.S. Provisional Application Ser. No. 60/424,698 filed Nov. 8, 2002 and U.S. Provisional Application Ser. No. 60/467,571 filed May 5, 2003, and the present application is a Continuation-In-Part of U.S. Non-Provisional application Ser. No. 10/235,846 filed Sep. 6, 2002, which in turn claims priority to U.S. Provisional Application No. 60/317,486 filed Sep. 7, 2001 and U.S. Provisional Application Ser. No. 60/342,854 filed Dec. 28, 2001. Each of the above applications is hereby incorporated herein by reference in its entirety.

FIELD OF THE INVENTION

The present invention relates to a headgear connection assembly for use in removably attaching a headgear assembly to a frame of a respiratory mask assembly, the mask assembly being used for treatment, e.g., of Sleep Disordered Breathing (SDB) with Non-invasive Positive Pressure Ventilation (NPPV).

BACKGROUND OF THE INVENTION

Respiratory mask assemblies used in the treatment of SDB may comprise a nasal mask designed to fit over a patient's nose, or a full face mask designed to fit over the nose and mouth of the patient. Air or other breathable gas is supplied by a blower and passed along a flexible conduit to the mask assembly.

The mask assembly generally comprises a relatively rigid shell, e.g., a frame, which defines a rearwardly opening cavity covering the patient's nose and/or mouth, and a soft portion, e.g., a cushion, which spaces the frame away from the face of the patient for comfortable contact.

The mask assembly is usually held in place using a headgear assembly, the frame and headgear assembly being joined using some form of connector.

One form of known connector is described in U.S. Pat. No. 6,374,826 (Gunaratnam et al.). The contents of this patent are hereby incorporated by reference.

Some patients have poor dexterity, and hence find certain arrangements of connectors awkward or difficult to use. For example, some patients may have difficulty in correctly joining the frame and headgear assembly with the connector. As a result, the connector may disengage during use or may become stuck so it becomes difficult for the patient to disconnect the frame from the headgear assembly.

Furthermore, some connectors are positioned on the frame of the mask assembly which makes it difficult for the user to see the connectors, because they are very close to the eyes or out of the range of vision of the patient. Hence, it is important to have a connector which is easy to use and which is easy to correctly assemble even if it is out of the range of vision of the patient.

SUMMARY OF THE INVENTION

One aspect of the present invention is to provide a respiratory mask assembly having a headgear connection assembly positioned between the frame and headgear assembly in a convenient and intuitive location for quick attachment and/or detachment by the patient, while not being easily detached accidentally.

Another aspect of the present invention provides a respiratory mask assembly for delivering breathable gas to a patient. The respiratory mask assembly according to one embodiment includes a frame and at least one locking clip. The frame has a main body and a side frame member provided on each lateral side of the main body. At least one of the side frame members includes an integrally formed locking clip receiver assembly. The at least one locking clip has a main body providing a front portion and a rear portion. The front portion is adapted to be removably coupled with the at least one locking clip receiver assembly and the rear portion is adapted to be removably coupled to a headgear assembly. The rear portion of the locking clip includes a cross bar that forms an opening through which a strap of the headgear assembly can pass and be removably coupled with the cross bar, and the front portion of the locking clip includes at least one resiliently flexible spring arm that is flexible within the plane of the main body.

Another aspect of the invention is to provide a headgear connection assembly which can be easily molded in a mask frame which includes a swivel elbow connector.

Other aspects, features and advantages of this invention will become apparent from the following detailed description when taken in conjunction with the accompanying drawings, which are a part of this disclosure and which illustrate, by way of example, principles of this invention.

BRIEF DESCRIPTION OF THE DRAWINGS

The accompanying drawings facilitate an understanding of the various embodiments of this invention. In such drawings:

FIG. 15 is a top view of the locking clip shown in FIG. 13;

FIG. 16 is a cross-section taken along line 16-16 of FIG. 15;

FIG. 17 is a front view of the locking clip shown in FIG. 13;

FIG. 18 is a rear view of the locking clip shown in FIG. 13;

FIG. 19 is a side view of the locking clip shown in FIG. 13;

DETAILED DESCRIPTION OF ILLUSTRATED EMBODIMENTS

Figure 1:
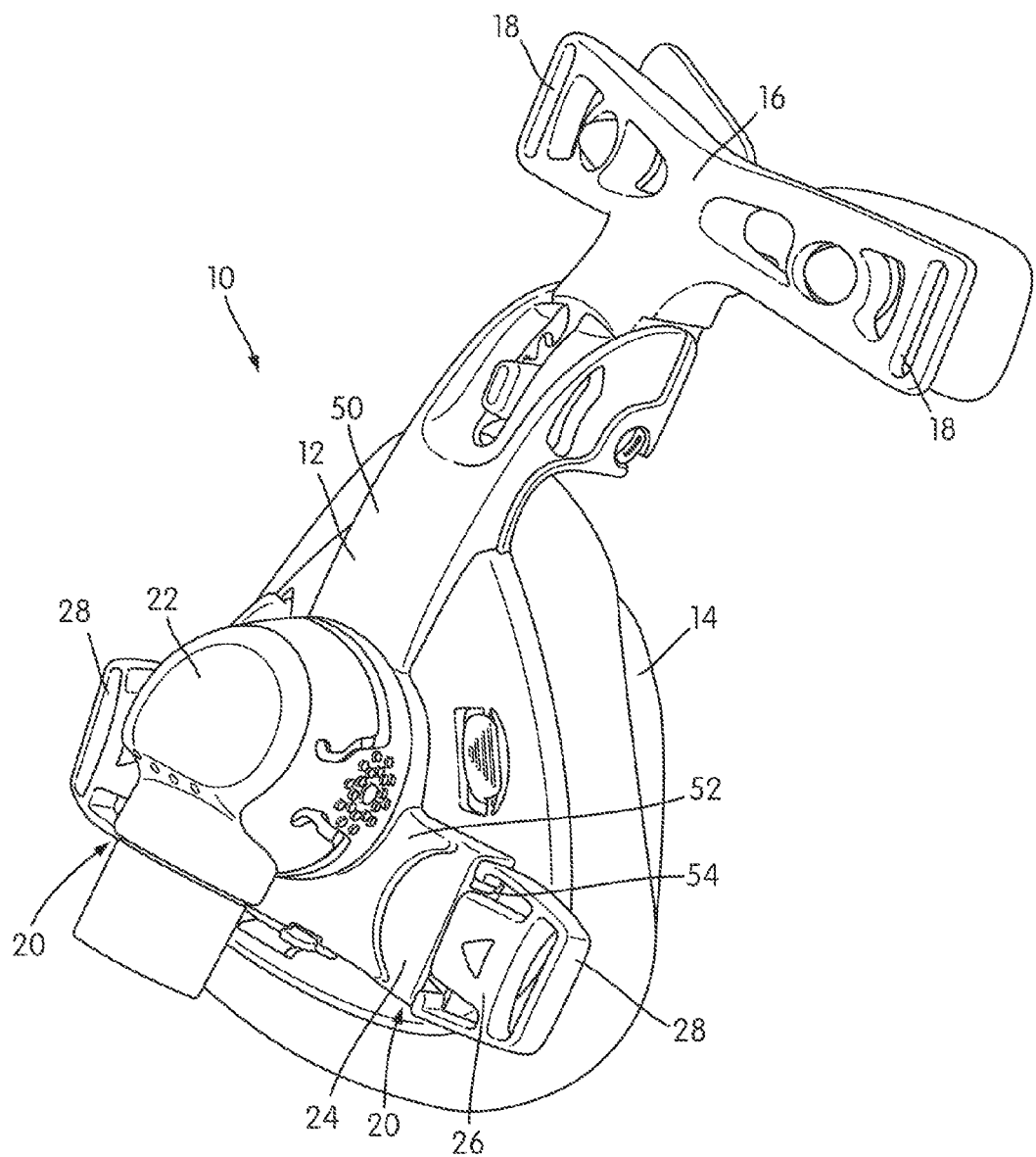
FIG. 1 is a front perspective view illustrating a mask assembly having a headgear connection assembly constructed in accordance with an embodiment of the invention.
Figure 2:
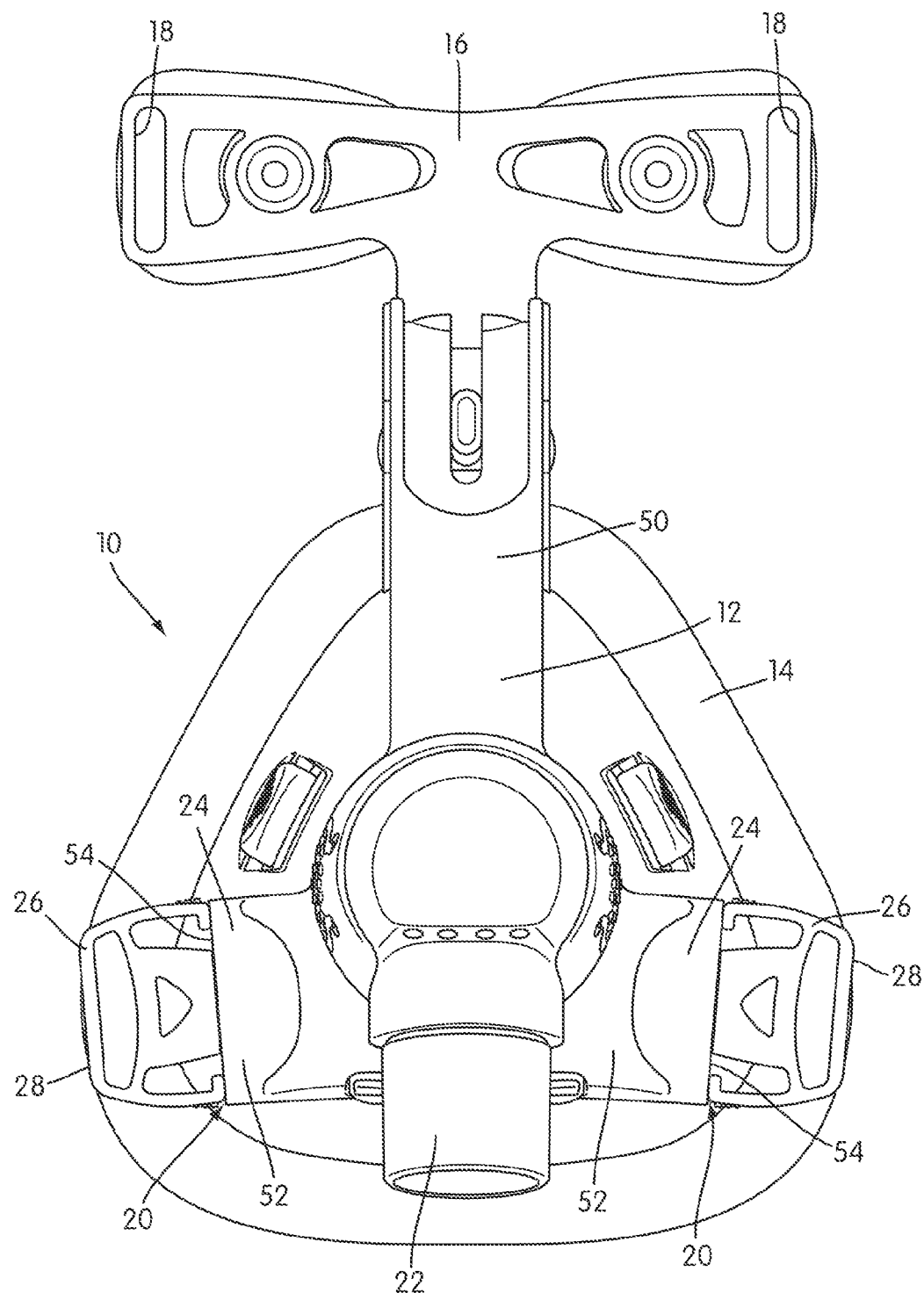
FIG. 2 is a front view of the mask assembly showing FIG. 1.

FIGS. 1 and 2 shown a respiratory mask assembly 10 that includes a frame 12 and a cushion 14 that may be permanently or removably connected to the frame 12. For example, the cushion 14 may be removably attached to the frame 12 with a cushion clip, straps, a friction or interference fit, and/or a tongue-in-groove arrangement, as is known in the art. However, the cushion 14 may be permanently attached to the frame 12 with glue and/or mechanical fastening means, for example.

A forehead support 16 is movably mounted to an upper portion of the frame 12. A headgear assembly (not shown) can be removably attached to the frame 12 to maintain the frame 12 and cushion 14 in a desired adjusted position on the patient's face. For example, the headgear assembly may include a pair of upper and lower straps with the upper straps removably connected to clip structures 18 provided on the forehead support 16 and the lower straps removably connected the frame 12 by a headgear connection assembly 20, as will be further discussed below.

In the illustrated embodiment, the mask assembly 10 is a nasal mask structure to deliver breathable gas to a patient's nose. However, the mask assembly 10 may be a nasal and mouth mask, or the mask assembly may be a full face mask.

A swivel elbow assembly 22 is removably attached to a front portion of the frame 12. The elbow assembly 22 is structured to be connected to a conduit that is connected to a pressurized supply. The pressurized supply supplies pressurized breathable gas through the conduit and elbow assembly 22 and into the cushion 14 for breathing by the patient.

In the illustrated embodiment, lower straps of the headgear assembly are removably attached to the frame 12 by a headgear connection assembly 20. The headgear connection assembly 20 includes a first connector portion 24 provided by the frame 12 and a second connector portion 26 adapted to be removably coupled with the first connector portion 24. The second connector portion 26 is removably connected to the lower straps of the headgear assembly.

Figure 3:
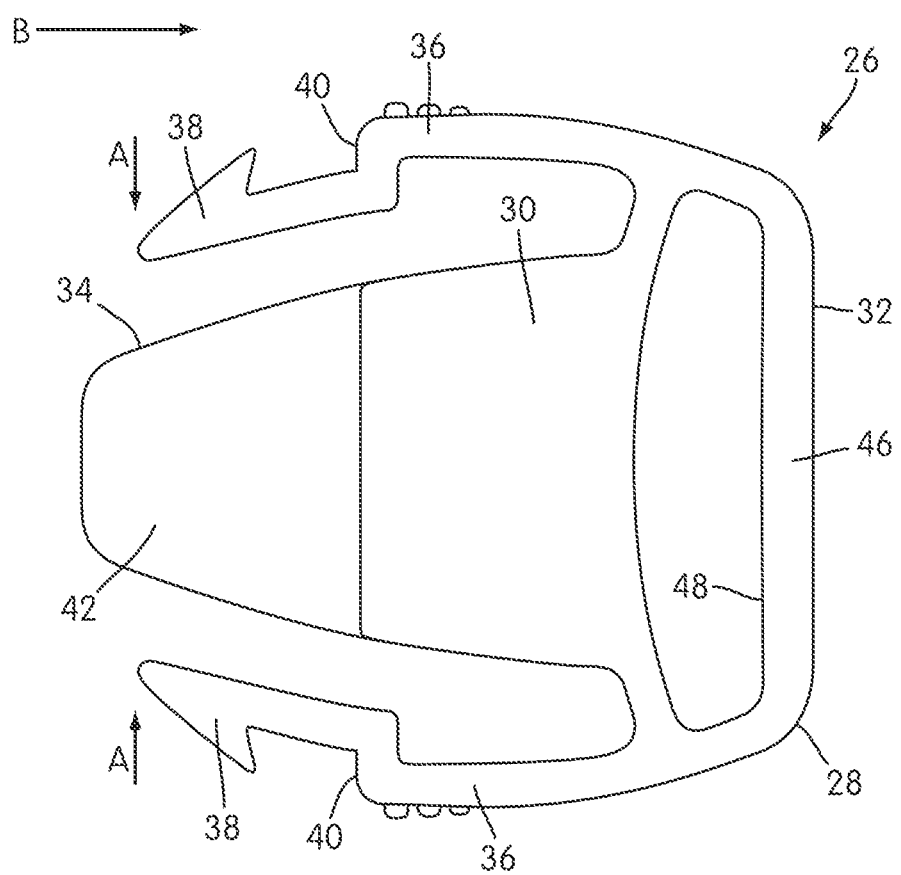
FIG. 3 is a top view of a locking clip of the headgear connection assembly shown in FIG. 1.
Figure 4:
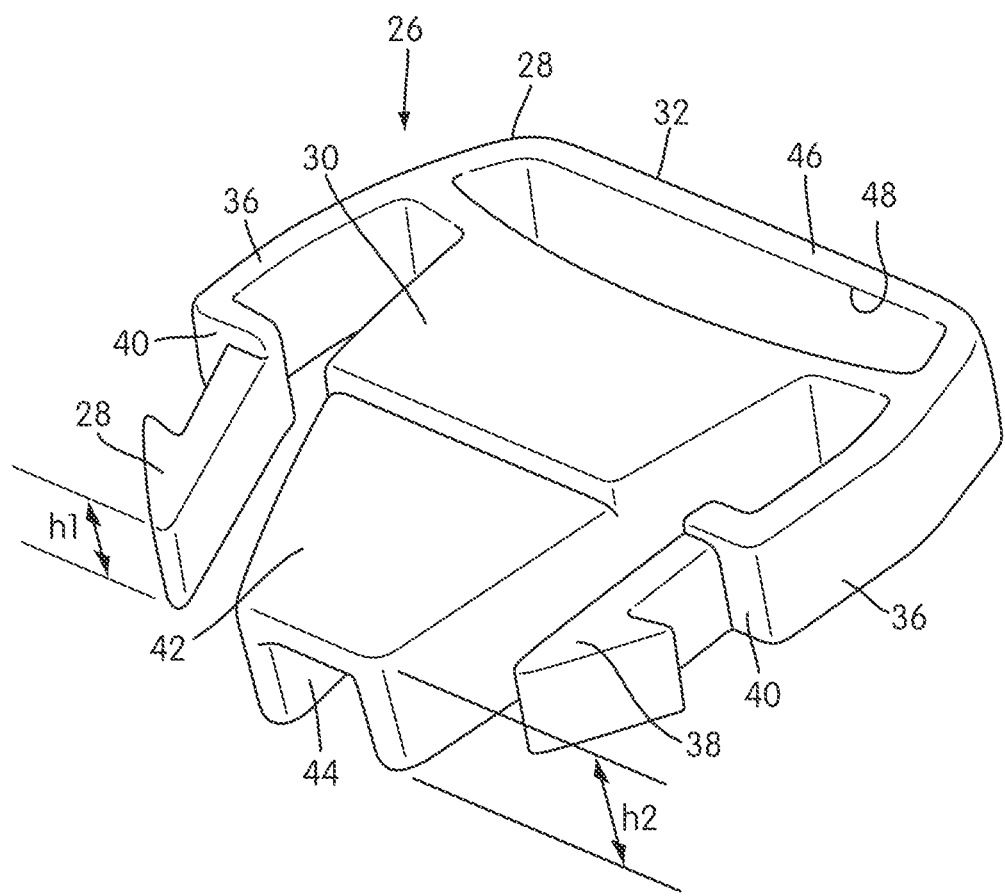
FIG. 4 is a perspective view of a locking clip of the headgear connection assembly shown in FIG. 1.

As shown in FIGS. 1-2, the second connector portion 26 includes a pair of locking clips 28. In a preferred embodiment, the locking clip 28 is a unitary plastic piece formed by injection molding. As shown in FIGS. 3 and 4, each locking clip 28 includes a main body 30 having a rear portion 32 and a front portion 34. The rear portion 32 is removably connected to a lower strap of the headgear assembly and the front portion 34 is removably coupled with the first connector portion 24 provided on the frame 12.

Specifically, the front portion 34 includes at least one and preferably two resiliently flexible spring arms 36 that are attached to opposite sides of the main body 30 and extend away from the main body 30 in a generally parallel manner. However, the front portion 34 may include one spring arm 36. The spring arms 36 can flex up and down, e.g., in the direction of arrows A or in a reverse direction of arrows A, respectively, as shown in FIG. 3. A locking tab 38 is attached to a free end of each spring arm 36. Further, each spring arm 36 is configured to provide a shoulder portion 40. In use, the shoulder portions 40 and locking tabs 38 are adapted to engage with corresponding portions of the first connector portion 24 for coupling the first and second connector portions 24, 26 with one another. For example, the locking tabs 38 are structured to prevent accidental disengagement of the second connector portion 26 from the first connector portion 24 if a force is applied to the second connector portion 26 in the direction of arrow B (FIG. 3), as will be further discussed.

The front portion 32 also includes a central support tab 42 positioned between the pair of spring arms 36. In the illustrated embodiment, the central support tab 42 has a length that is greater than the length of each of the spring arms 36. The central support tab 42 is slidably insertable into a complimentary shaped portion of the first connector portion 24, as will be further discussed.

As shown in FIG. 4, the central support tab 42 includes a groove 44. The central support tab 42 has a height of h2, and the front portion of each spring arm 36 has a height of h1. In the illustrated embodiment, the height h2 is larger than the height h1. In an alternative embodiment, h2 may be smaller than h1.

The rear portion 32 of the second connector portion 26 includes a cross bar 46 that forms an opening 48 through which a lower strap of the headgear assembly may pass and be removably connected. Specifically, an end portion of the lower strap of the headgear assembly may be wrapped around the cross bar 46. Fastening of the lower strap to the cross bar 46 may be assisted by use of a hook and loop material, such as Velcro®. Thus, the lower strap may be adjusted with respect to the locking clip 28 for proper fit. The locking clip 28 may be rotatably adjustable with respect to the headgear assembly, e.g., see U.S. Provisional Application No. 60/402,509, filed on Aug. 12, 2002, incorporated herein by reference in its entirety.

Figure 5:
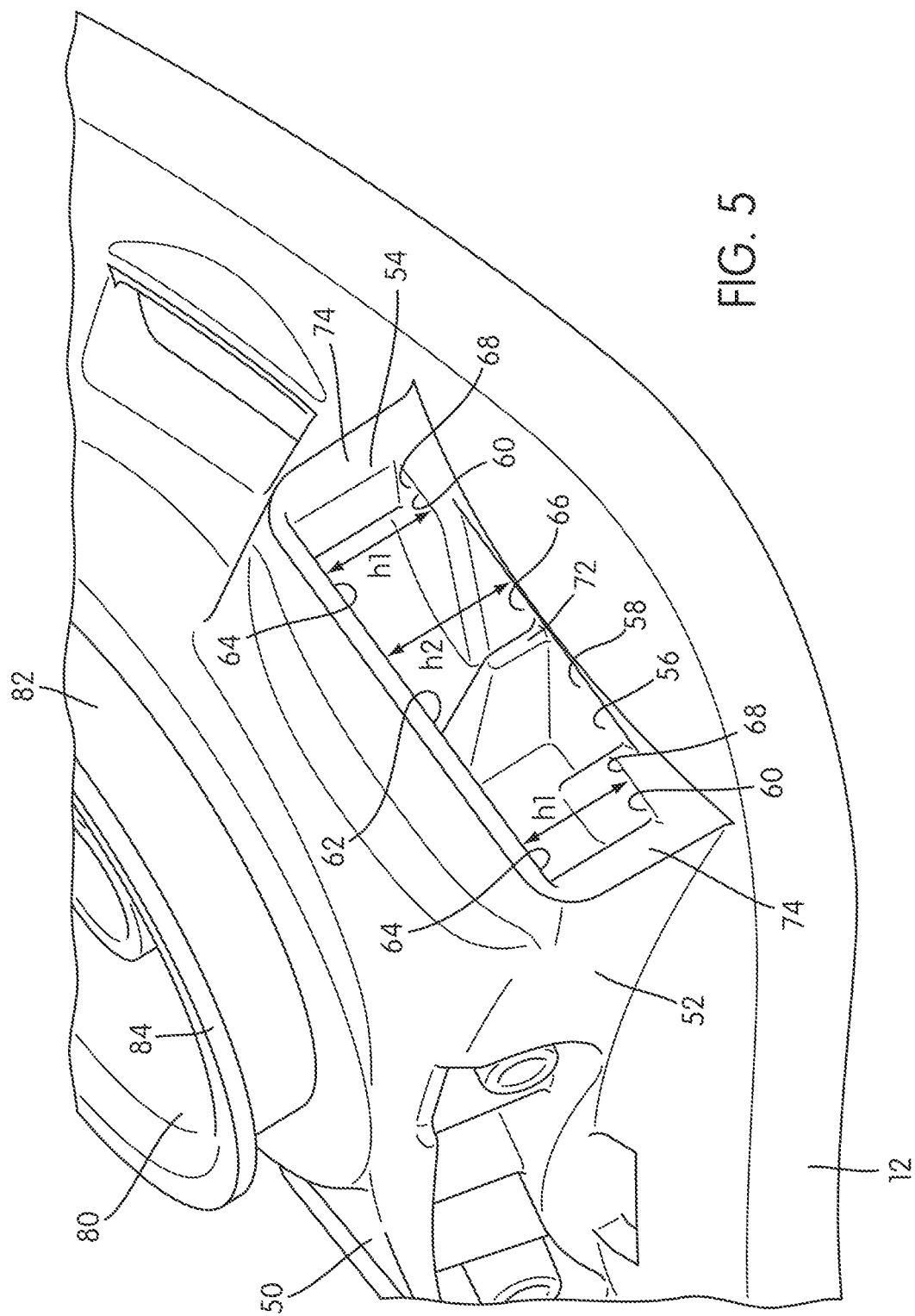
FIG. 5 is a perspective view of a locking clip receiver assembly of the headgear connection assembly shown in FIG. 1.
Figure 6:
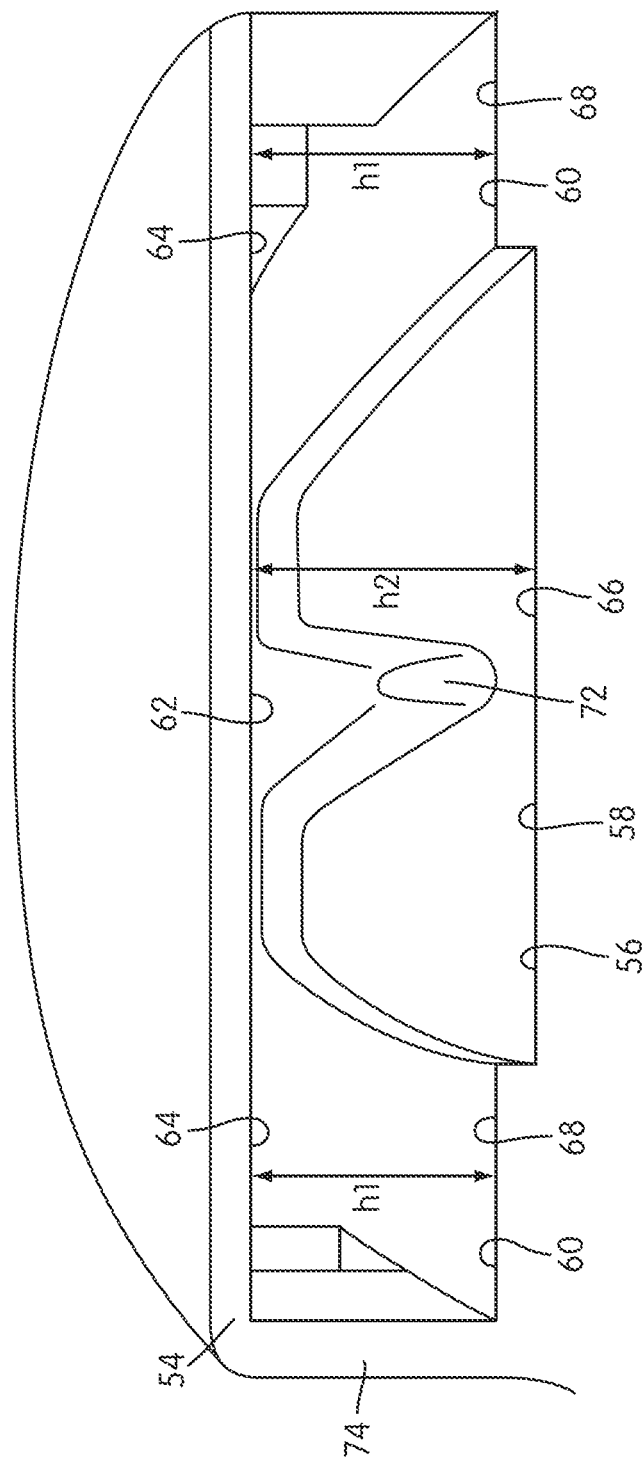
FIG. 6 is a front view of a locking clip receiver assembly of the headgear connection assembly shown in FIG. 1.
Figure 7:
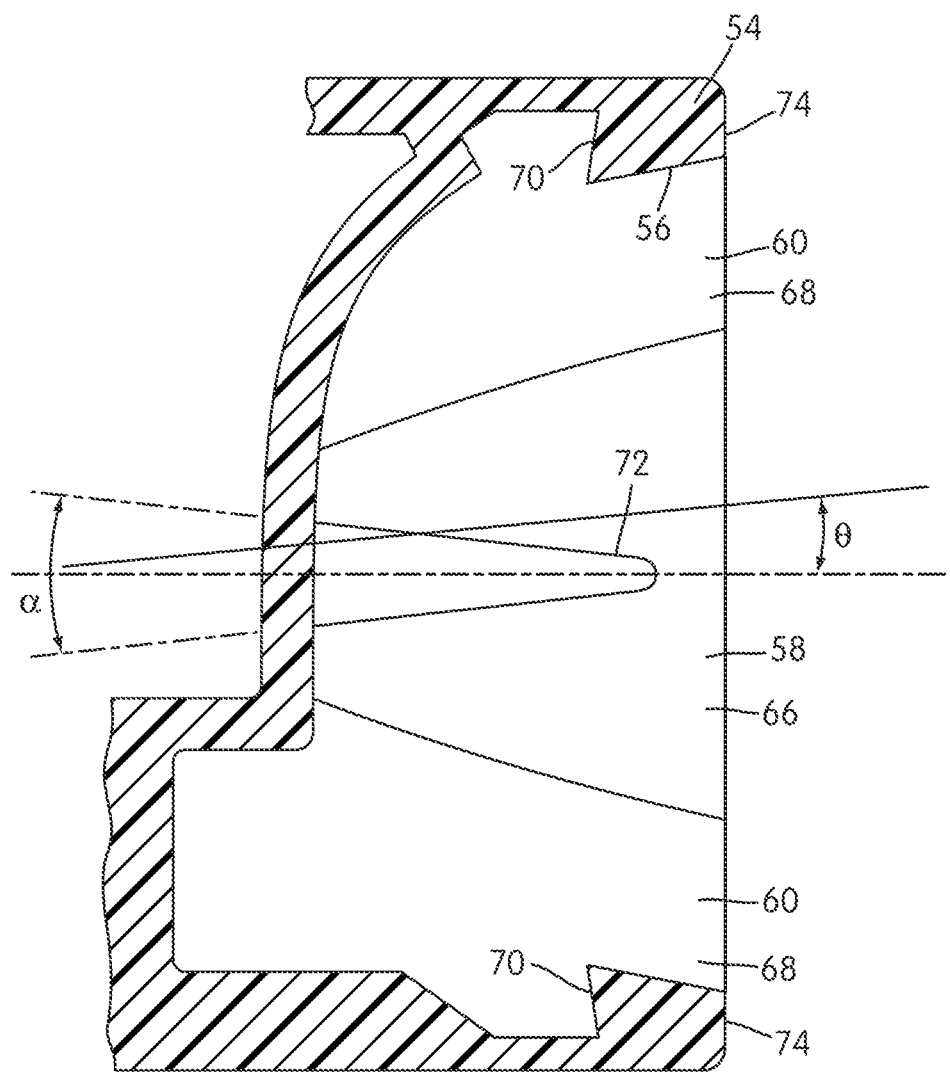
FIG. 7 is a cross-sectional view of a locking clip receiver assembly of the headgear connection assembly shown in FIG. 1.

As shown in FIGS. 1, 2, and 5, the frame 12 includes a main body 50 accommodating the cushion 14 and a side frame member 52 provided on each lateral side of the main body 50. Each side frame member 52 includes the first connector portion 24 which is integrally formed therewith. As shown in FIGS. 5-7, the first connector portion 24 includes a locking clip receiver assembly 54. The locking clip 28 is structured to interlock with the locking clip receiver assembly 54 to removably attach the locking clip 28, and hence the headgear assembly, to the frame 12.

Each locking clip receiver assembly 54 includes a slot 56 having a central portion 58 and two locking portions 60 positioned on opposite sides of the central portion 58. The central portion 58 of the slot 56 has an upper surface 62 that is continuous with an upper surface 64 of each of the locking portions 60. However, lower surfaces 66, 68 of the central portion 58 and two locking portions 60, respectively, have a stepped configuration. Specifically, as shown in FIGS. 5 and 6, the central portion 58 has a height h2 between the upper surface 62 and lower surface 66 thereof. The two locking portions 60 have a height h1 between the upper surface 64 and lower surface 68 thereof. In the illustrated embodiment, the height h2 is greater than the height h1. Moreover, the height h2 of the central portion 58 is approximately equal to the height h2 of the central support tab 42 and the height h1 of the two locking portions 60 is approximately equal to the height h1 of the front portion of each spring arm 36. This arrangement facilitates the connection between the locking clip 28 and the locking clip receiver assembly 54, as will be further discussed.

As shown in FIG. 7, each of the locking portions 60 includes a locking flange 70 positioned on an outer wall thereof for engagement with the locking tab 38 of a locking clip 28.

The central portion 58 includes a wall 72 that extends upwardly from the lower surface 66 towards the upper surface 62. In the illustrated embodiment, the wall 72 extends approximately half the way to the upper surface 62.

Figure 10:
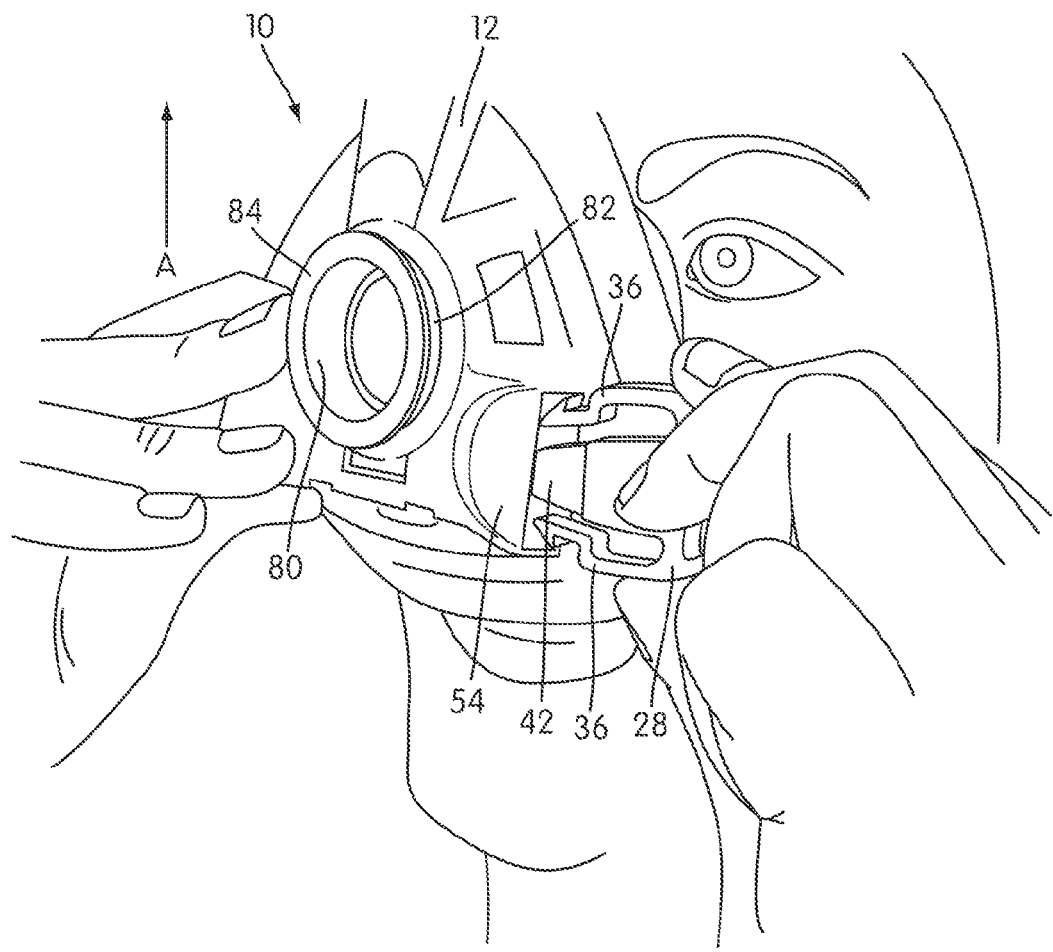
FIG. 10 is a perspective view illustrating the mask assembly of FIG. 1 being secured to a patient's face by a headgear connection assembly of FIG. 1.

In the illustrated embodiment, the first connector portions 24 are integrally molded with the frame 12. As shown in FIGS. 5 and 10, the frame 12 also includes an orifice 80 and collar 82 adapted to receive a swivel elbow 22 (FIGS. 1 and 2). The collar 82 has a rim 84 which extends horizontally and radially from the orifice 80. In order to form the collar 82, it is advantageous if the mold can be withdrawn horizontally. However, it is desirable that the headgear be presented at an angle with respect to the frame 12. The first connector portions 24 are aligned downwardly at an angle θ of approximately 5% with respect to the horizontal. When the frame 12 is molded, the mold components should be withdrawn in a horizontal direction to form the collar 82. As shown in FIG. 7, the junction between the lower surfaces 66, 68 of the central portion 58 and locking portions 60, respectively, is arranged to make an angle α which is sufficiently wide to enable the sides of the mold to be withdrawn in a horizontal direction. Further, the angled junction facilitates the connection between the locking clip 28 and the locking clip receiver assembly 54.

Figure 9:
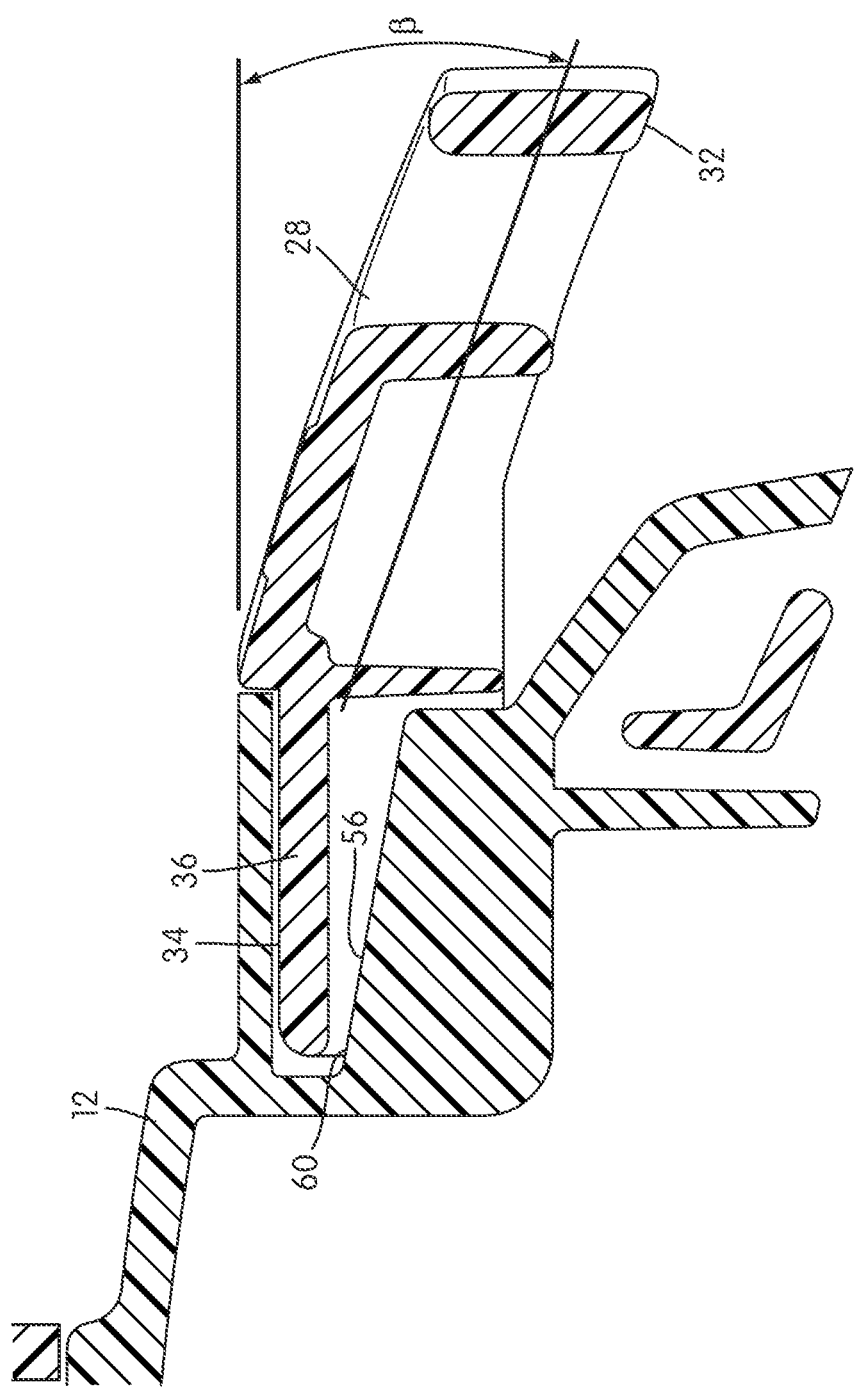
FIG. 9 is a cross-sectional view illustrating the engagement between a locking clip and a locking clip receiver assembly of the headgear connection assembly shown in FIG. 1.

As shown in FIG. 9, the front portion 34 and rear portion 32 of the locking clip 28 are disposed at an angle β with respect to one another. In the illustrated embodiment, the rear portion 34 is angled downwardly with respect to the horizontal, whereas the front portion 32 is generally horizontally aligned. By use of this angle, the locking clip 28 does not protrude as far from the mask as it would otherwise. Furthermore, the headgear straps are connected to the locking clip 28 at an angle which more naturally follows the contour of the face. In an alternative form of the invention, the front and rear portions 34, 32 may be curved to achieve an angular difference between the front and rear. An advantage of either approach is that the slot 56 of the first connector portion 24 into which the front portion 34 of the second connector 26 is slidably received may be generally horizontal. This is advantageous during the manufacture process because it means the sides of the mold may be withdrawn horizontally to assist formation of the collar 82.

Figure 8:
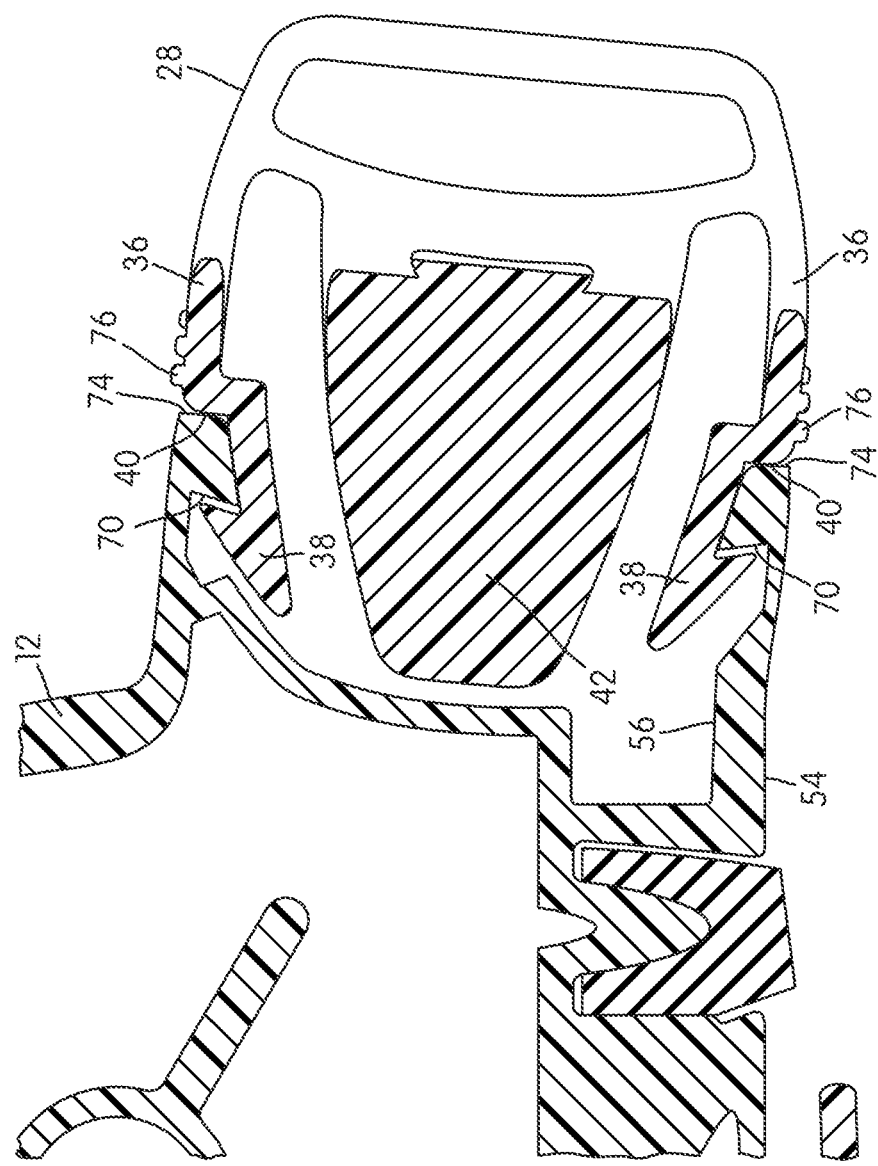
FIG. 8 is a cross-sectional view illustrating the engagement between a locking clip and a locking clip receiver assembly of the headgear connection assembly shown in FIG. 1.

As shown in FIGS. 8-9, the locking portions 60 of the slot 56 are adapted to receive a respective one of the pair of spring arms 36, the locking tab 38 of each spring arm 36 interlocking with the locking flange 70 provided in respective locking portions 60 to removably attach the locking clip 28, and hence the headgear assembly, to the frame 12. The shoulder portion 40 of each locking clip 28 engages an engagement face 74 provided on the frame 12 when the locking clip 28 is inserted into the locking clip receiver assembly 54 to provide additional support for the locking clip 28. The locking tab 38 may interlock with an undercut provided in the locking portions 60 to removably attach the locking clip 28 to the frame 12. Further, each locking tab 38 may extend through a slot provided in the outer wall of the locking portion 60. The slot need not extend through the outer wall of the locking portion 60.

The central support tab 42 is inserted into the central portion 58 of the slot 56 when the locking clip 28 and locking clip receiver assembly 54 are engaged so as to prevent relative movement between the locking clip 28 and the locking clip receiver assembly 54.

Specifically, when the locking clip 28 is inserted into the locking clip receiver assembly 54, the spring arms 36 are forced toward one another (in the direction of arrows A as shown in FIG. 3) as the locking tabs 38 are inserted into respective locking portions 60 of the slot 56 and ride up and over the locking flanges 70. Once the locking tabs 38 have cleared respective locking flanges 70, the spring arms 36 can spring outwardly (in the reverse direction of arrows A as shown in FIG. 3) to provide a locking engagement between the locking tabs 38 and the locking flanges 70. Sufficient clearance is provided in the locking portions 60 of the slot 56 to allow the necessary movement of the locking tabs 38 to clear the locking flanges 70.

The central support tab 42 is configured to have a close fit with the central portion 58 of the slot 56 so that when the central support tab 42 is inserted into the central portion 58, little rotational, rocking or side-to-side movement is permitted between the locking clip 28 and the locking clip receiver assembly 54. The central support tab 42 is longer than the spring arms 36 to assist with alignment into the slot 56. Further, the groove 44 of the central support tab 42 engages the wall 72 provided in the central portion 58 of the slot 56 to facilitate entry of the central support tab 42 into the central portion 58 of the slot 56. Alternatively, the central support tab 42 may have a protrusion that engages a groove provided in the central portion 58 of the slot 56. Also, the central support tab 42 has a shape that is complementary to the angle α that defines the shape of the central portion 58 of the slot 56.

Figure 11:
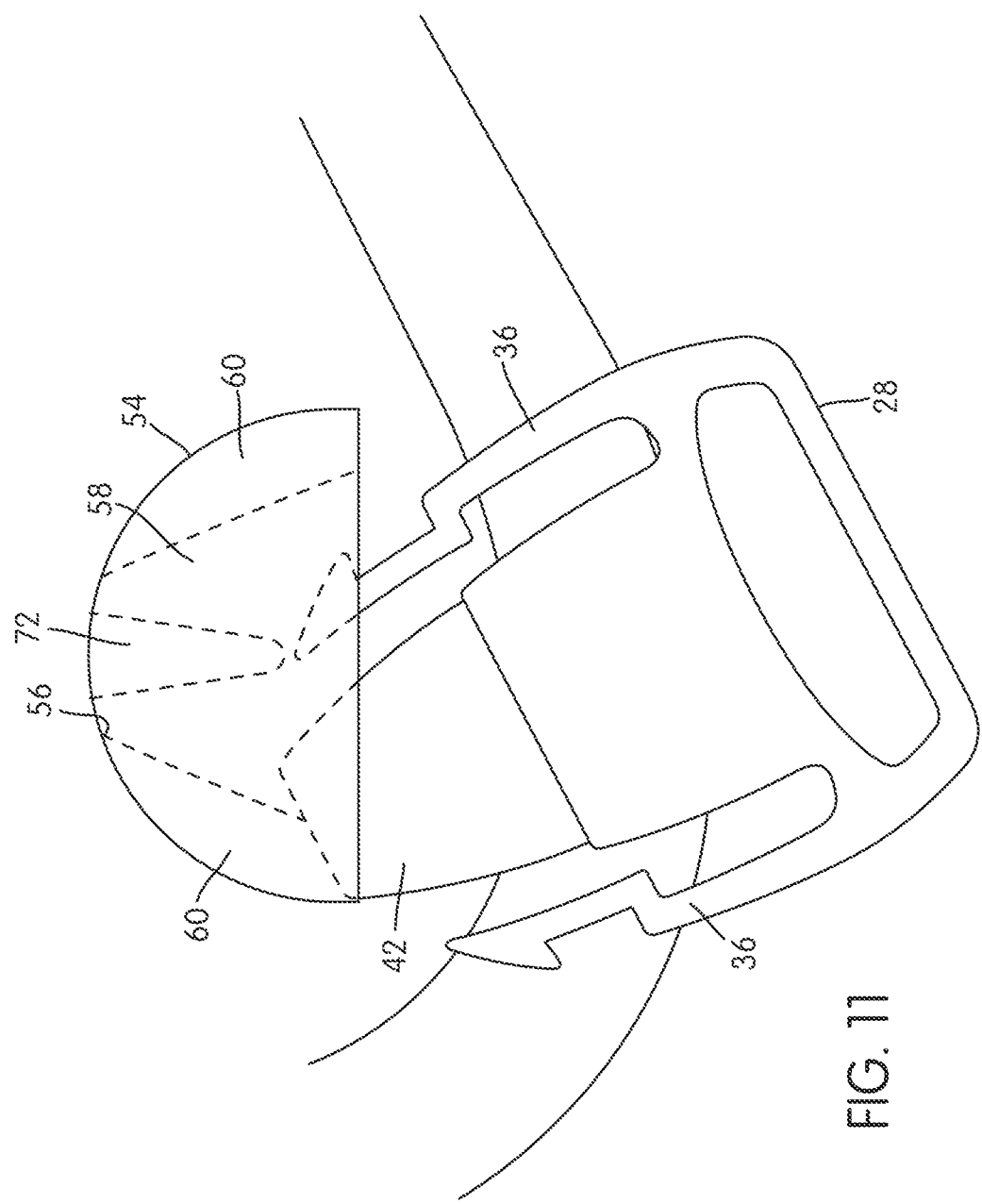
FIG. 11 is a top view illustrating the headgear connection assembly of FIG. 1 in a first incorrect position with respect to the frame of the mask assembly.
Figure 12:
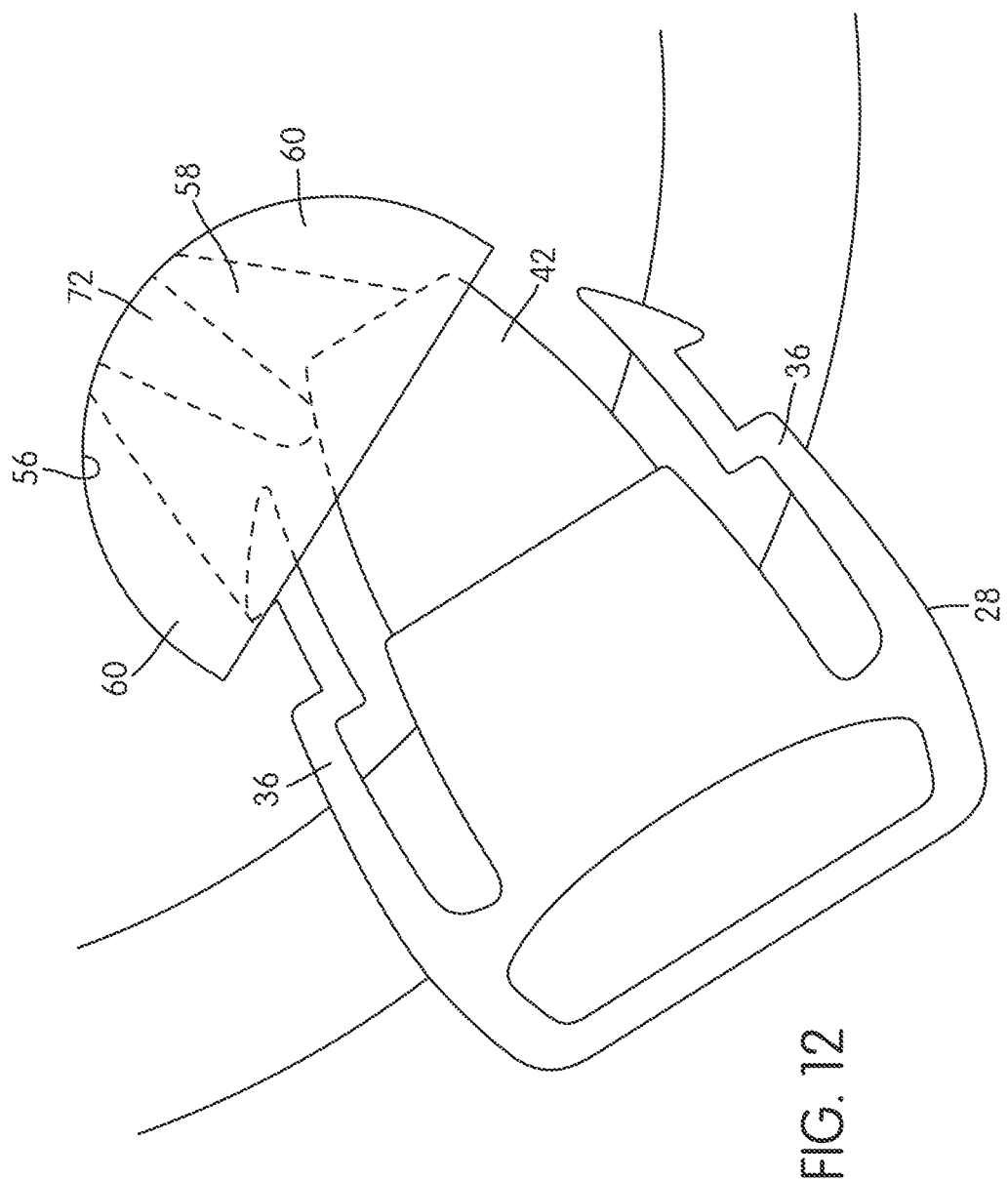
FIG. 12 is a top view illustrating the headgear connection assembly of FIG. 1 in a second incorrect position with respect to the frame of the mask assembly.
Figure 13:
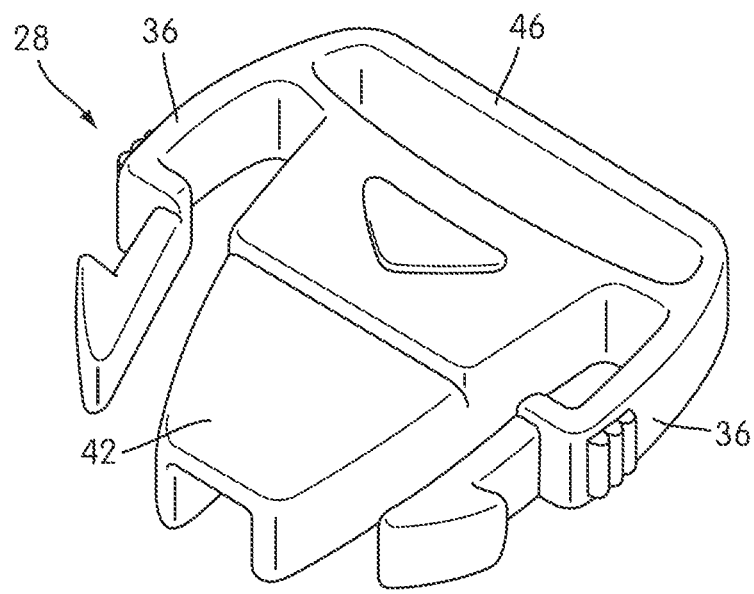
FIG. 13 is a front perspective view of a locking clip of the headgear connection assembly shown in FIG. 1.

Because the height h2 of the central portion 58 is approximately equal to the height h2 of the central support tab 42 and the height h1 of the two locking portions 60 is approximately equal to the height h1 of the front portion of each spring arm 36, the locking portions 60 of the slot 56 are of sufficient height to accommodate the front portion of each spring arm 36, but insufficient to accommodate the central support tab 42. That is, the central support tab 42 is too thick to fit into the locking portions 60 of the slot 56. Because of this arrangement, it will be clear to the patient whether or not the locking clip 28 has been correctly engaged with the locking clip receiver assembly 54. Thus, the patient cannot inadvertently partly assemble the locking clip 28 to the locking clip receiver assembly 54 in such a way that it will accidentally release. For example, FIG. 11 illustrates a first incorrect position of the locking clip 28 with respect to the locking clip receiver assembly 54 and FIG. 12 illustrates a second incorrect position of the locking clip 28 with respect to the locking clip receiver assembly 54. In both instances, the patient is unable to insert the thicker central support tab 42 into the thinner locking portion 60 of the slot 56.

To release the locking clip 28 from the locking clip receiver assembly 54, the patient simply forces the spring arms 36 towards one another to clear the locking tabs 38 from respective locking flanges 70. Then, the patient pulls the locking clip 28 outwardly away from the frame 12 to disengage the locking clip 28 from the locking clip receiver assembly 54.

As shown in FIG. 8, the locking tabs 38 and central support tab 42 have rounded or contoured edges to facilitate entry into the slot 56. Also, the outward surfaces of the locking clip 28 and the frame 12 preferably form a generally coextensive continuous surface, which is not interrupted when connected. Preferably, the locking clip 28 is as wide as the side frame members 52, which facilitates tactile location of the locking clip 28 by the patient.

The spring arms 36 are designed to flex within the plane of the locking clip main body 30, which further improves the ease by which the locking clips 28 are attached and detached. This positioning improves the ergonomics of flexing the spring arms up and down. As shown in FIG. 10, the patient's thumb and opposing finger can be used to readily locate and operate the locking clips 28. The outward surface of the spring arms 36 may include a series of protrusions 76 to facilitate gripping of the locking clip 28 by the patient (see FIG. 8). Further, the locking clips 28 are connected to the straps of the headgear assembly so that length adjustment may be provided.

An advantage of the headgear connection assembly 20 is that one locking clip 28 can be used with the locking clip receiver assembly 54 provided on each side frame member 52, thereby reducing manufacturing costs and the need for inventory.

FIGS. 13-20 show further structural details in various dimensions in one embodiment of the locking clip 28 of the headgear connection assembly 20. For example, the locking clip 28 has a length in the range of 20-40 mm, preferably 29 mm, a width in the range of 20-40 mm, preferably 27.8 mm, and a height in the range of 4-8 mm, preferably 6.7 mm. In an embodiment of the locking clip 28, the dimensions illustrated in FIGS. 13-20 may vary ±10%.

In the illustrated embodiment, the rear portion 32 of the locking clip 28 includes a cross-bar 46 that forms an opening 48 through which a strap of the headgear assembly can be removably coupled with the cross-bar 46. In other forms of the invention, the strap of the headgear assembly is connected using other mechanisms. For example, the strap may include a hook which engages with a corresponding hole in the locking clip. In another form, the strap is sewn in position and is not removable. In another form, the strap is removable, and held in position by a friction fit.

In the illustrated embodiment, a locking clip in accordance with the invention is used only on a mask frame adjacent a swivel elbow, in the region of the mouth; and straps for connection to a forehead support of the mask assembly are held in position only by hook & loop material. Thus two locking clips are used on one mask. In another embodiment of the invention, four locking clips are used, two as illustrated, and a further two being used as part of the forehead support.

FIGS. 21-28 illustrate another embodiment of a locking clip, indicated as 228. As shown in FIGS. 29-40, the locking clip 228 is structured for use with a full-face mask assembly having a frame 212 (see FIGS. 29-34) and a forehead support 216 (see FIGS. 35-40). Specifically, as shown in FIGS. 29-34, the frame 212 has a pair of locking clip receiver assemblies 254 structured to interlock with a pair of locking clips 228. As shown in FIGS. 35-40, the forehead support 216 has a pair of locking clip receiver assemblies 254 structured to interlock with a pair of locking clips 228. However, the locking clip 228 and locking clip receiver assemblies 254 illustrated may be structured for use with a nasal mask or a nasal and mouth mask, for example.

As shown in FIGS. 21-28, the locking clip 228 is substantially similar to the locking clip 28 described above. In contrast, the length of the groove 244 provided in clip 228 is greater than the length of the groove 44 provided in clip 28, as will be further discussed. The remaining elements of the locking clip 228 are similar to the elements of the locking clip 28 and are indicated with similar reference numerals.

Similar to the previous embodiment, the locking clip 228 includes a main body 230 having a rear portion 232 and a front portion 234. The rear portion 232 is removably connected to a strap of the headgear assembly and the front portion 234 is removably coupled with a respective locking clip receiver assembly 254 provided on the frame 212 or forehead support 216. The front portion 234 includes two resiliently flexible spring arms 236 that are attached to opposite sides of the main body 230. The flexible spring arms 236 are flexible within the plane of the main body 230.

Figure 22:
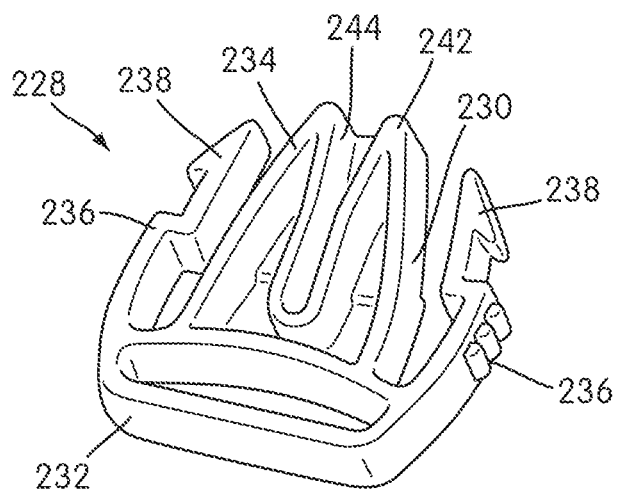
FIG. 22 is a rear perspective view of the locking clip shown in FIG. 21.
Figure 23:
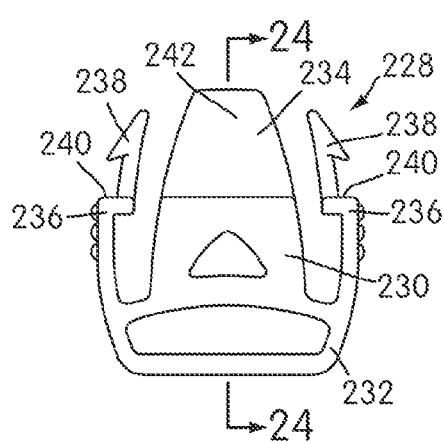
FIG. 23 is a top view of the locking clip shown in FIG. 21.
Figure 24:
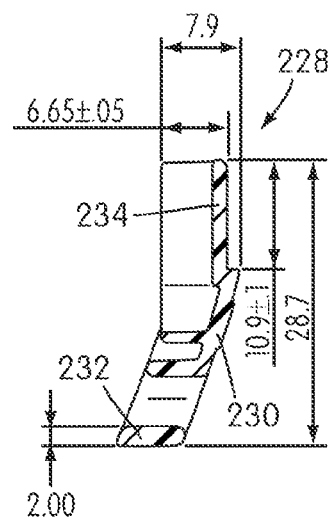
FIG. 24 is a cross-section taken along line 24-24 of FIG. 23.
Figure 25:
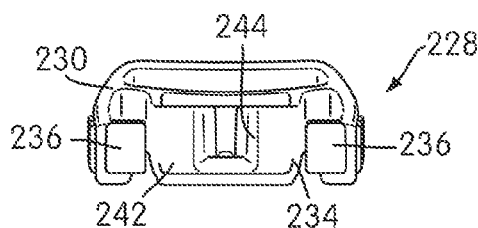
FIG. 25 is a front view of the locking clip shown in FIG. 21.
Figure 26:
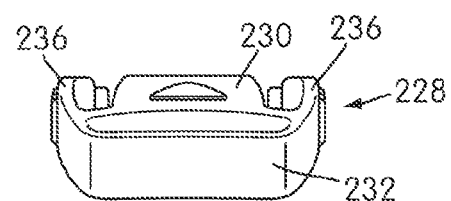
FIG. 26 is a rear view of the locking clip shown in FIG. 21.
Figure 27:
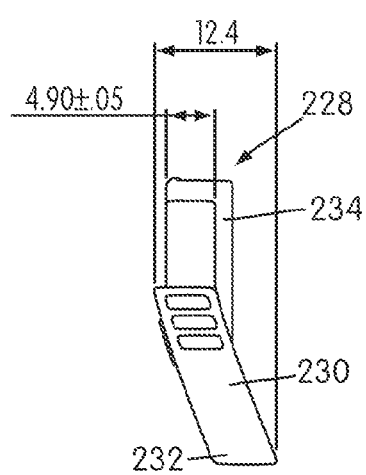
FIG. 27 is a side view of the locking clip shown in FIG. 21.
Figure 28:
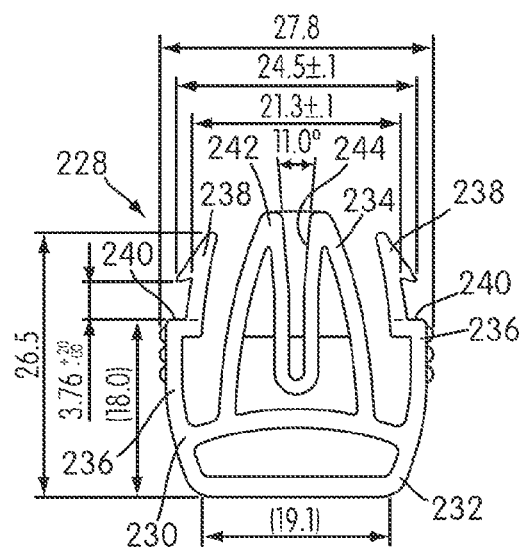
FIG. 28 is a bottom view of the locking clip shown in FIG. 21.

Further, each spring arm 236 includes a locking tab 238 and a shoulder portion 240 adapted to engage with a respective locking clip receiver assembly 254 provided on the frame 212 or forehead support 216. As best shown in FIGS. 22 and 28, the front portion 234 also includes a central support tab 242 that includes a groove 244.

Figure 14:
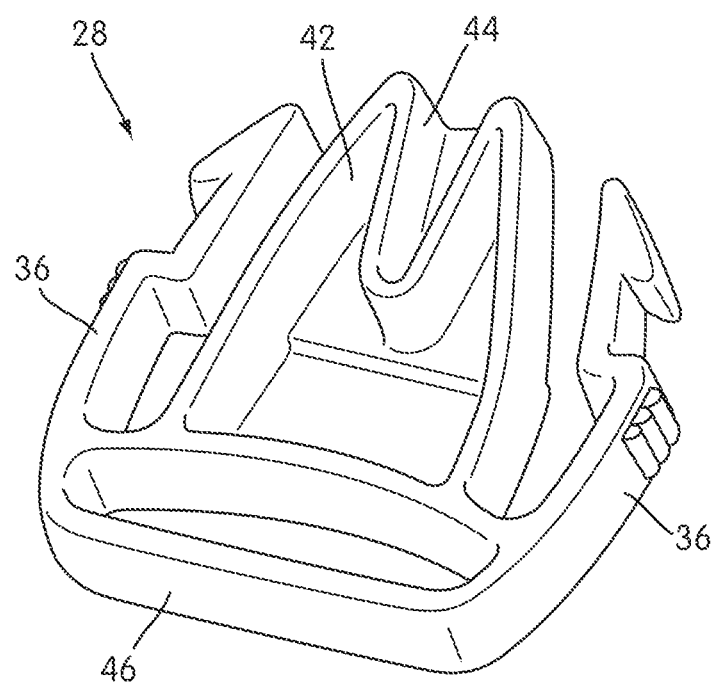
FIG. 14 is a rear perspective view of the locking clip shown in FIG. 13.
Figure 20:
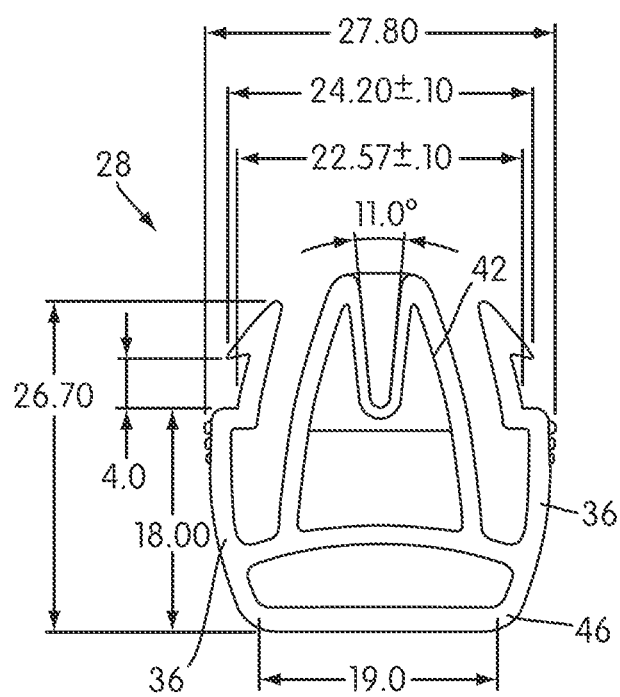
FIG. 20 is a bottom view of the locking clip shown in FIG. 13.
Figure 21:
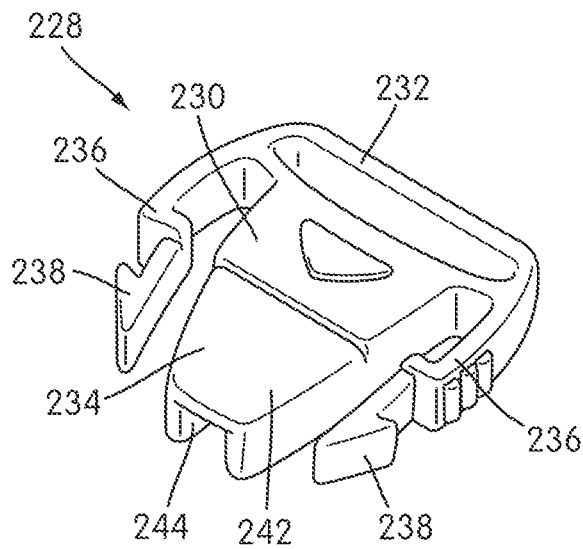
FIG. 21 is a front perspective view of another embodiment of a locking clip.

The groove 244 provided in clip 228 is deeper or more elongated than the groove 44 provided in clip 28 (as best shown in FIGS. 14 and 22). In the illustrated embodiment, the groove 244 has a length that is at least half a length of the central support tab 242. The elongated groove in clip 228 facilitates with alignment of the clip 228 with the frame 212 or forehead support 216. Moreover, the elongated groove 244 helps to prevent relative movement between the locking clip 228 and the respective locking clip receiver assembly 254 on the frame 212 or forehead support 216, as will be further discussed below.

FIGS. 29-34 show an embodiment of a frame 212 for a full-face mask assembly. The frame 212 may be permanently or removably connected to a cushion (not shown) in any suitable manner. Further, a swivel elbow assembly (not shown) may be removable attached to a front portion of the frame 212.

Each lateral side of the frame 212 includes a locking clip receiver assembly 254 structured to interlock with a locking clip 228. Similar to locking clip receiver assembly 54, the locking clip receiver assembly 254 includes a slot 256 having a central portion 258 and two locking portions 260. The locking portions 260 include a locking flange 270 (see FIG. 32) positioned on an outer wall thereof for engagement with the locking tab 238 of a locking clip 228. In the illustrated embodiment, an upper wall 261 of the slot 256 includes a pair of openings 263 that are aligned with the locking flange 270. This enables the patient to visually confirm that the locking tab 238 of a locking clip 228 is interlocked with the locking flange 270 in use.

Figure 30:
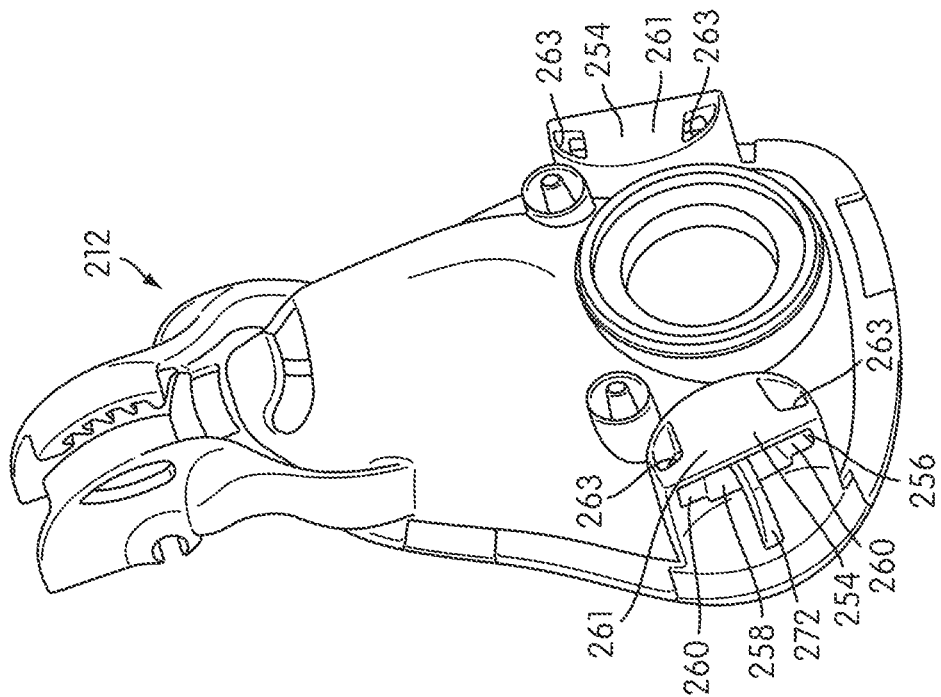
FIG. 30 is a front perspective view, similar to FIG. 29 but at a different angle, of the frame shown in FIG. 29.
Figure 29:
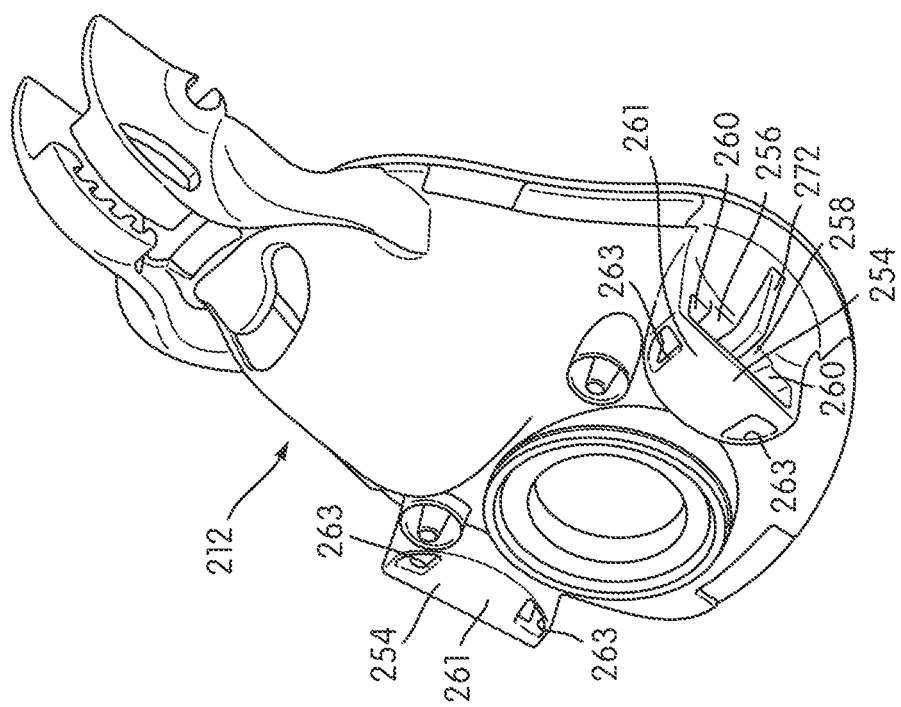
FIG. 29 is a front perspective view illustrating an embodiment of a frame for a full-face mask assembly, the frame having a locking clip receiver assembly structured to interlock with the locking clip shown in FIG. 21.
Figure 31:
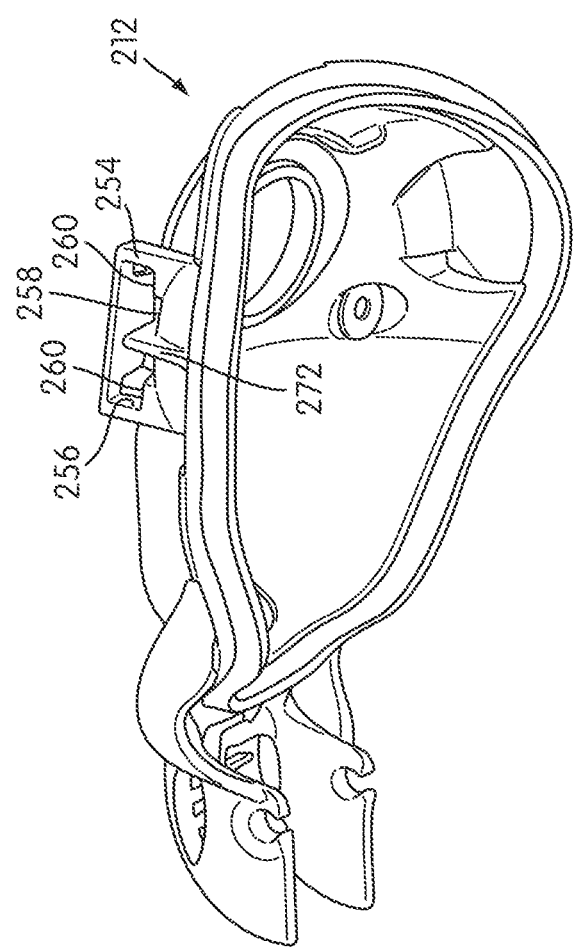
FIG. 31 is a rear perspective view of the frame shown in FIG. 29.
Figure 32:
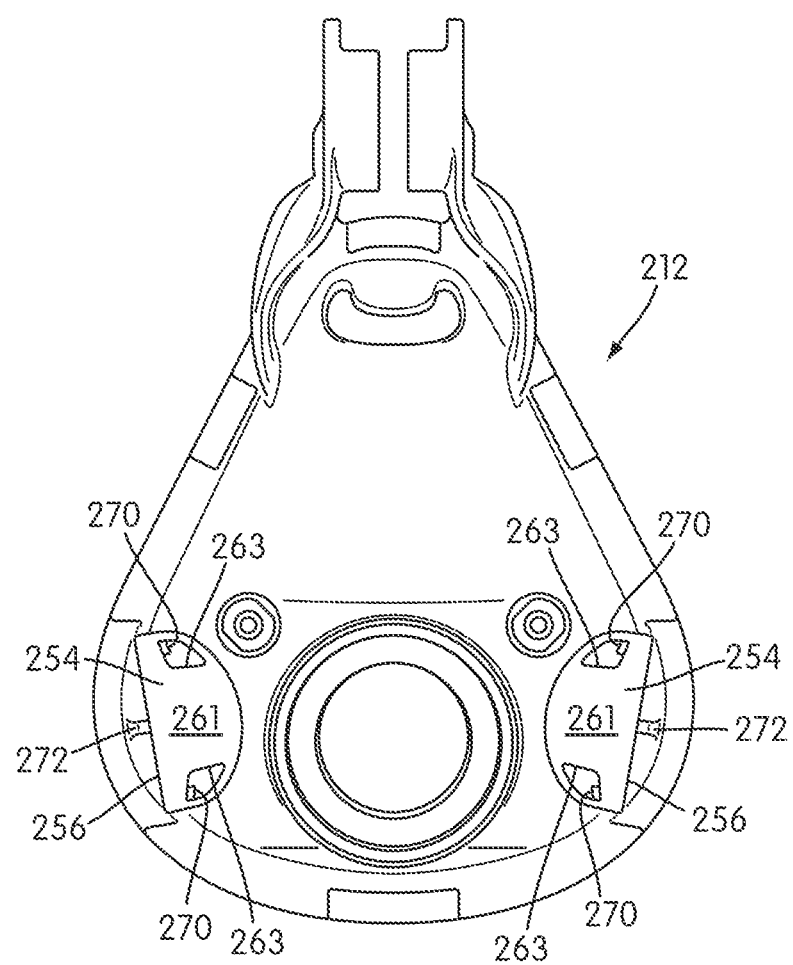
FIG. 32 is a front view of the frame shown in FIG. 29.
Figure 33:
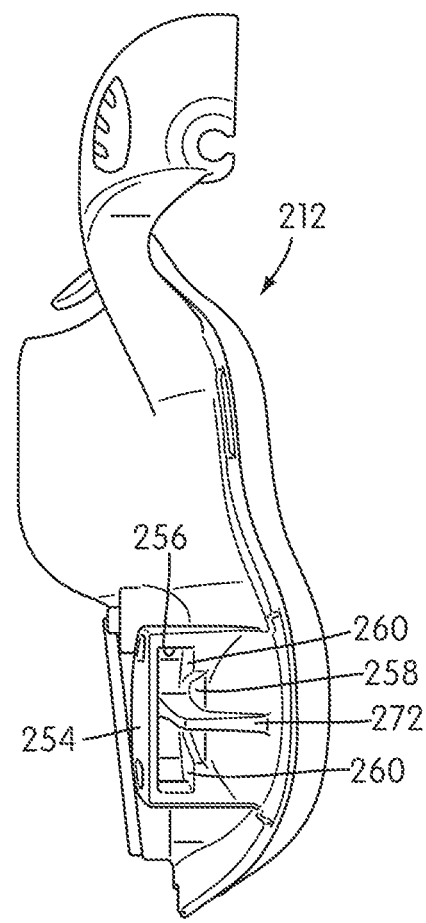
FIG. 33 is a side view of the frame shown in FIG. 29.
Figure 34:
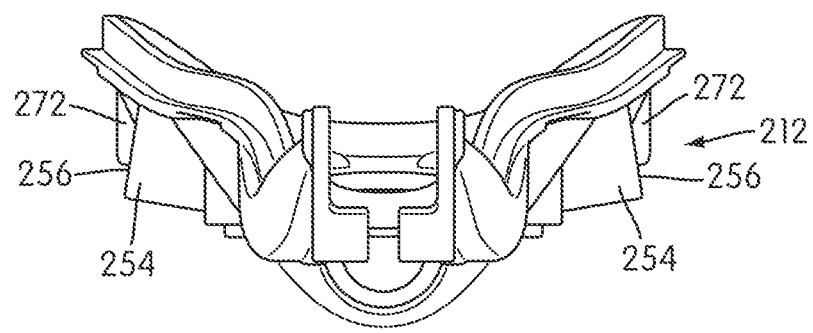
FIG. 34 is a top view of the frame shown in FIG. 29.
Figure 35:
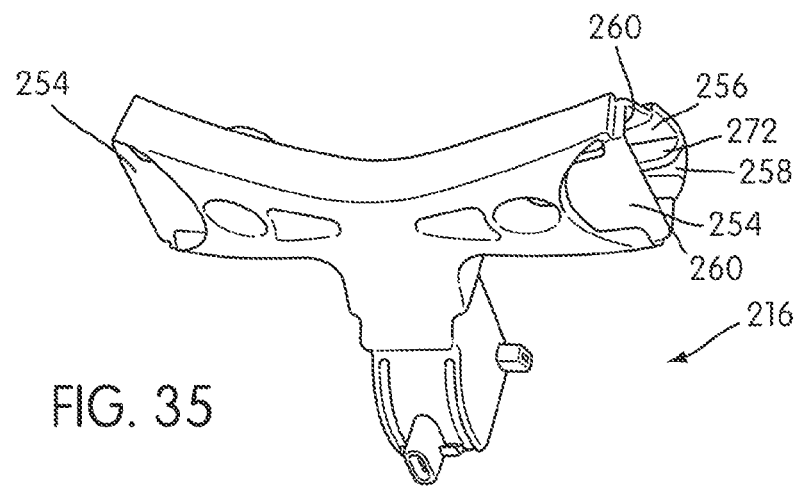
FIG. 35 is a top perspective view illustrating an embodiment of a forehead support adapted to be movably mounted to an upper portion of the frame shown in FIG. 29, the forehead support having a locking clip receiver assembly structured to interlock with the locking clip shown in FIG. 21.
Figure 36:
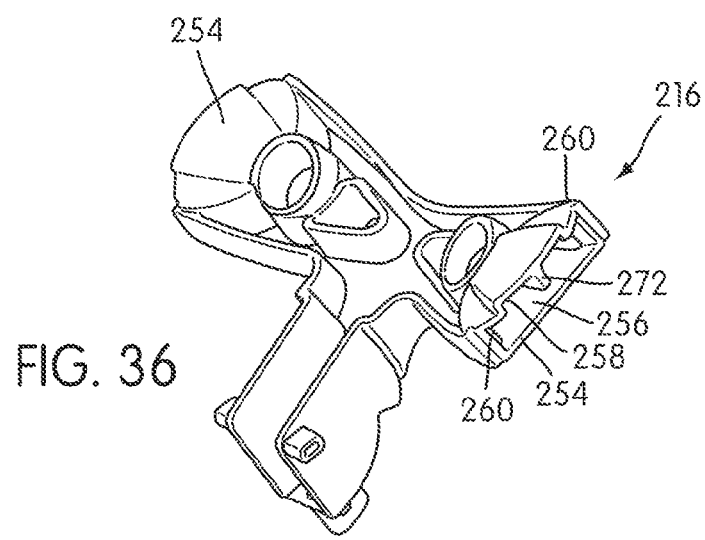
FIG. 36 is a rear perspective view of the forehead support shown in FIG. 35.
Figure 37:
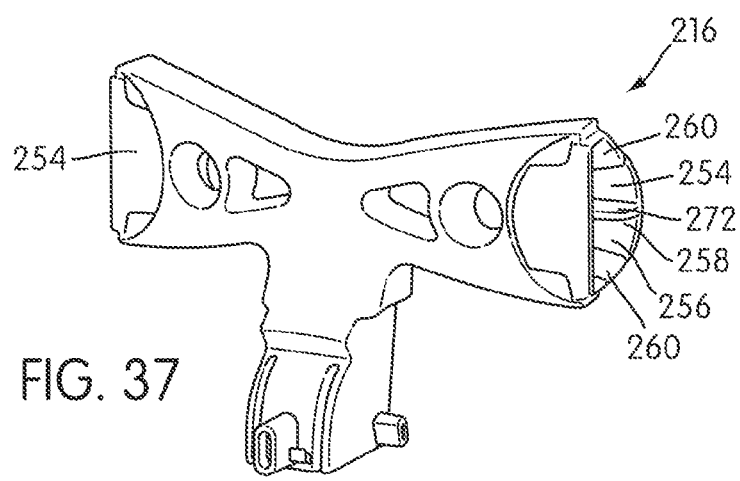
FIG. 37 is a front perspective view of the forehead support shown in FIG. 35.
Figure 38:
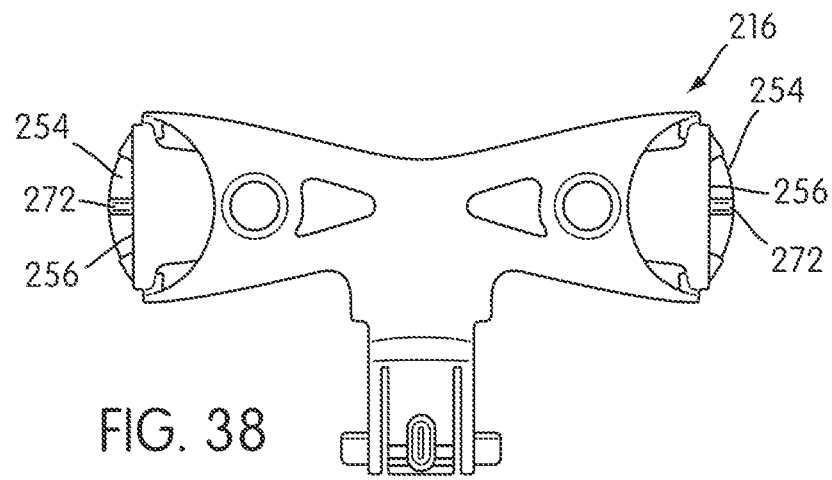
FIG. 38 is a front view of the forehead support shown in FIG. 35.
Figure 39:
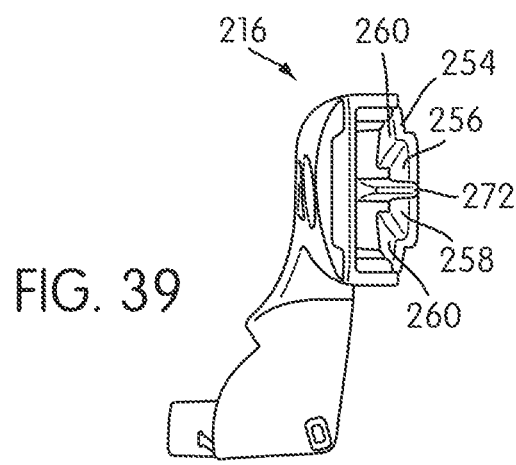
FIG. 39 is a side view of the forehead support shown in FIG. 35.
Figure 40:
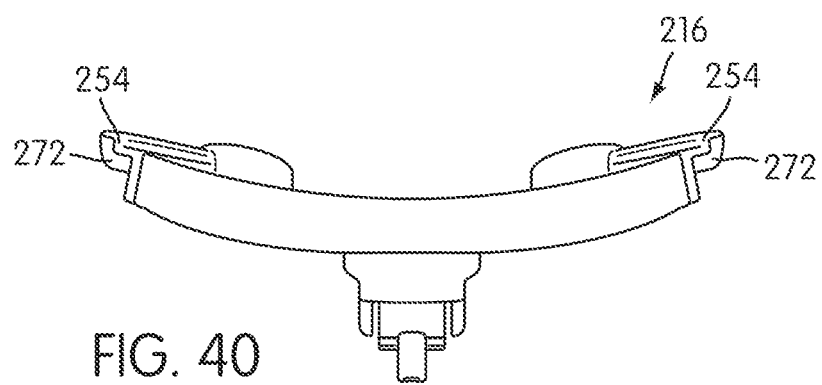
FIG. 40 is a top view of the forehead support shown in FIG. 35.

Also, the central portion 258 includes a wall 272. As best shown in FIGS. 29, 30, and 32, the wall 272 provided in the locking clip receiver assembly 254 extends outwardly away from the slot 256. In the embodiment of locking clip receiver assembly 54, the wall 72 was positioned entirely within the slot 56 (see FIGS. 5, 7, 11, and 12). The elongated wall 272 of locking clip receiver assembly 254 facilitates alignment of a clip 228 with a respective locking clip receiver assembly 254. Specifically, the groove 244 of a clip 228 may be engaged with the elongated wall 272 so as to guide the clip 228 into the slot 256.

Moreover, when a clip 228 is engaged with a respective locking clip receiver assembly 254, the engagement between the elongated groove 244 of the clip 228 and the wall 272 of the locking clip receiver assembly 254 prevents rocking or side-to-side movement between the clip 228 and locking clip receiver assembly 254. Further, any force applied to one of the spring arms 236 of the clip 228, when the clip 228 is engaged with the locking clip receiver assembly 254, will not be transferred to the other spring arm 236 of the clip 228. Thus, the clip 228 is prevented from being inadvertently disengaged from the respective locking clip receiver assembly 254 in use. To release the locking clip 228 from the locking clip receiver assembly 254, both spring arms 236 must be forced towards one another to clear the locking tabs 238 form respective locking flanges 270.

FIGS. 35-40 show an embodiment of a forehead support 216 adapted to be movably mounted to an upper portion of the frame 212. The forehead support 216 may be permanently or removably connected to a forehead pads (not shown) in any suitable manner.

Each lateral side of the forehead support 216 includes a locking clip receiver assembly 254 structured to interlock with a locking clip 228. The locking clip receiver assembly 254 on the forehead support 216 is substantially similar to the locking clip receiver assembly on the frame 216 and indicated with similar reference numerals. As a result, one locking clip 228 can be used with the locking clip receiver assemblies 254 provided on the frame 212 and the forehead support 216, thereby reducing manufacturing costs and the need for inventory. Thus, four locking clips 228 are used, two locking clips 228 for the frame 212 and two locking clips 228 for the forehead support 216. In use, upper straps of a headgear assembly would be removably connected to the locking clips 228 for the forehead support 216 and lower straps of the headgear assembly would be removably connected to locking clips 228 for the frame 212.

It can thus be appreciated that the aspects of the present invention have been fully and effectively accomplished. The foregoing specific embodiments have been provided to illustrate the structural and functional principles of the present invention, and are not intended to be limiting. To the contrary, the present invention is intended to encompass all modifications, alterations and substitutions within the spirit and scope of the detailed description.

What is claimed is:

1. A respiratory mask assembly for delivering breathable gas to a patient, comprising:
   a frame having a main body and a side frame member provided on each lateral side of the main body,
   the main body providing an orifice therethrough for the introduction of breathable gas into a nasal breathing cavity and a collar that substantially surrounds the orifice,
   at least one of the side frame members including an integrally formed locking clip receiver assembly,
   wherein the frame is formed by molding such that mold components of a mold can be withdrawn along a single plane to separate the mold from the collar and the locking clip receiver assembly,
   wherein the locking clip receiver assembly includes a slot adapted to receive a locking clip, the slot having a central portion and two locking portions on opposite sides of the central portion, and
   wherein the central portion has a lower central portion surface and each of the two locking portions has a lower locking portion surface, and a junction between the lower central portion surface and each lower locking portion surface is arranged to include a stepped configuration, and the stepped configuration is angled to enable the mold components to be withdrawn along the single plane.

2. The respiratory mask assembly according to claim 1, further comprising an elbow assembly adapted to be coupled to the collar.

3. The respiratory mask assembly according to claim 1, wherein the slot extends generally horizontally so as to enable the mold components to be withdrawn horizontally.

4. The respiratory mask assembly according to claim 1, wherein the locking clip includes a main body providing a front portion and a rear portion, the front portion adapted to be removably coupled with the locking clip receiver assembly and the rear portion adapted to be removably coupled to a headgear assembly.

5. The respiratory mask assembly according to claim 4, wherein the front portion and the rear portion are disposed at an angle β to one another, and the front portion is generally horizontally aligned.

6. The respiratory mask assembly according to claim 4, wherein the slot extends generally horizontally and adapted to receive the front portion of the locking clip.

7. The respiratory mask assembly according to claim 4, wherein the rear portion of the locking clip includes a cross bar that forms an opening through which a strap of the headgear assembly can pass and be removably coupled with the cross bar, and the front portion of the locking clip includes at least one resiliently flexible spring arm that is flexible within a plane of the main body.

8. The respiratory mask assembly according to claim 1, wherein the collar has a rim which extends horizontally and radially from the orifice.

9. The respiratory mask assembly according to claim 1, wherein the central portion includes a wall that extends upwardly from the lower central portion surface.

10. The respiratory mask assembly according to claim 1, wherein the central portion has an upper central portion surface that is continuous with an upper locking portion surface of each of the two locking portions.

11. The respiratory mask assembly according to claim 1, wherein the central portion of the slot includes a height that is greater than a height of each of the two locking portions of the slot.

12. The respiratory mask assembly according to claim 1, wherein the slot includes a front opening, and the lower central portion surface and each lower locking portion surface extends rearwardly from the front opening into an interior of the slot.

13. The respiratory mask assembly according to claim 1, wherein the stepped configuration is angled in relation to a direction of insertion of the locking clip into the slot.

14. A method for molding a frame for a respiratory mask assembly, the method comprising:
   molding a frame in a mold to include a main body and a side frame member provided on each lateral side of the main body, the main body defining an orifice therethrough and a collar that substantially surrounds the orifice;
   forming a locking clip receiver assembly on at least one of the side frame members; and
   withdrawing opposed mold components of the mold along a single plane to separate the mold from the collar and the locking clip receiver assembly,
   wherein the locking clip receiver assembly includes a slot adapted to receive a locking clip, the slot having a central portion and two locking portions on opposite sides of the central portion, and
   wherein the central portion has a lower central portion surface and each of the two locking portions has a lower locking portion surface, and a junction between the lower central portion surface and each lower locking portion surface is arranged to include a stepped configuration, and the stepped configuration is angled to enable the mold components to be withdrawn along the single plane.

15. The method according to claim 14, wherein the collar is adapted to receive an elbow assembly.

16. The method according to claim 14, wherein the slot extends generally horizontally so as to enable the mold components to be withdrawn horizontally.

17. The method according to claim 14, wherein the locking clip receiver is adapted to be removably coupled to a front portion of the locking clip.

18. The method according to claim 14, wherein the collar has a rim which extends horizontally and radially from the orifice.

19. The method according to claim 14, wherein the central portion includes a wall that extends upwardly from the lower central portion surface.

* * * * *